(12) United States Patent
Adams et al.

(10) Patent No.: US 10,580,525 B2
(45) Date of Patent: Mar. 3, 2020

(54) SECURE CABINET FOR DISPENSING ITEMS

(71) Applicant: Peacock Law P.C., Albuquerque, NM (US)

(72) Inventors: Patrick Adams, Kamuela, HI (US); William E. Bell, Albuquerque, NM (US)

(73) Assignee: Peacock Law P.C., Albuquerque, NM (US)

( * ) Notice: Subject to any disclaimer, the term of this patent is extended or adjusted under 35 U.S.C. 154(b) by 0 days.

(21) Appl. No.: 15/387,023

(22) Filed: Dec. 21, 2016

(65) Prior Publication Data

US 2017/0103185 A1   Apr. 13, 2017

Related U.S. Application Data

(63) Continuation of application No. 14/923,949, filed on Oct. 27, 2015, now Pat. No. 9,665,690, which is a
(Continued)

(51) Int. Cl.
| | | |
|---|---|---|
| *G07F 17/00* | (2006.01) | |
| *G16H 20/10* | (2018.01) | |
| *G06F 19/00* | (2018.01) | |
| *E05G 1/06* | (2006.01) | |
| *G07F 9/02* | (2006.01) | |
| *G07F 11/00* | (2006.01) | |
| *G07F 11/62* | (2006.01) | |

(Continued)

(52) U.S. Cl.
CPC ............ *G16H 20/10* (2018.01); *A61J 7/0084* (2013.01); *A61J 7/0481* (2013.01); *E05B 39/04* (2013.01); *E05B 45/06* (2013.01); *E05B 49/00* (2013.01); *E05B 65/0075* (2013.01); *E05G 1/04* (2013.01); *E05G 1/06* (2013.01); *E05G 1/10* (2013.01); *G05B 19/124* (2013.01); *G06F 19/00* (2013.01); *G06F 19/3462* (2013.01); *G06K 7/10762* (2013.01); *G06Q 10/087* (2013.01); *G07F 5/18* (2013.01); *G07F 9/026* (2013.01); *G07F 11/002* (2013.01); *G07F 11/62* (2013.01); *G07F 17/0092* (2013.01); *E05F 15/00* (2013.01); *E05G 1/08* (2013.01); *E05Y 2400/80* (2013.01)

(58) Field of Classification Search
CPC .................................................. G07F 17/0092
USPC .................................................. 700/231–244
See application file for complete search history.

(56) References Cited

U.S. PATENT DOCUMENTS

| | | | |
|---|---|---|---|
| 3,593,881 A | * | 7/1971 | Paap ........................ G07D 1/04 221/15 |
| 4,847,764 A | | 7/1989 | Halvorson |

(Continued)

FOREIGN PATENT DOCUMENTS

| | | |
|---|---|---|
| JP | 54-122196 | 9/1979 |
| JP | 60-181479 | 9/1985 |

*Primary Examiner* — Timothy R Waggoner
(74) *Attorney, Agent, or Firm* — Peacock Law P.C.; Justin R. Jackson; Deborah A. Peacock

(57) ABSTRACT

A secure cabinet that can secure and distribute products. The cabinet can have a user interface that receives information about a user and the user's identity can then be authenticated. The cabinet can accept a user's request to dispense a product and, if the user is approved, the cabinet can dispense a quantity of product to the approved user.

29 Claims, 35 Drawing Sheets

Related U.S. Application Data continuation of application No. 13/589,012, filed on Aug. 17, 2012, now Pat. No. 9,171,415, which is a continuation-in-part of application No. 12/499,043, filed on Jul. 7, 2009, now abandoned.

(60) Provisional application No. 61/525,103, filed on Aug. 18, 2011, provisional application No. 61/134,034, filed on Jul. 7, 2008.

(51) Int. Cl.

| | | |
|---|---|---|
| *G07F 5/18* | (2006.01) | |
| *G05B 19/12* | (2006.01) | |
| *G06K 7/10* | (2006.01) | |
| *A61J 7/00* | (2006.01) | |
| *A61J 7/04* | (2006.01) | |
| *E05B 39/04* | (2006.01) | |
| *E05B 45/06* | (2006.01) | |
| *E05B 49/00* | (2006.01) | |
| *E05B 65/00* | (2006.01) | |
| *E05G 1/04* | (2006.01) | |
| *E05G 1/10* | (2006.01) | |
| *G06Q 10/08* | (2012.01) | |
| *E05G 1/08* | (2006.01) | |
| *E05F 15/00* | (2015.01) | |

(56) References Cited

U.S. PATENT DOCUMENTS

| | | | |
|---|---|---|---|
| 5,905,653 A | 5/1999 | Higham et al. | |
| 5,927,540 A | 7/1999 | Godlewski | |
| 5,986,219 A | 11/1999 | Carroll et al. | |
| 6,305,377 B1 | 10/2001 | Portwood et al. | |
| 6,330,491 B1 | 12/2001 | Lion | |
| 6,438,451 B1 | 8/2002 | Lion | |
| 6,587,031 B1 | 7/2003 | Daugherty et al. | |
| 6,694,221 B2 | 2/2004 | Chavez et al. | |
| 6,711,460 B1 | 3/2004 | Reese | |
| 6,760,643 B2 | 7/2004 | Lipps | |
| 6,814,254 B2 | 11/2004 | Life et al. | |
| 6,892,941 B2 | 5/2005 | Rosenblum | |
| 7,006,893 B2 | 2/2006 | Hart et al. | |
| 7,006,894 B2 | 2/2006 | De La Huerga | |
| 7,077,286 B2 | 7/2006 | Shows et al. | |
| 7,286,900 B1 | 10/2007 | Frederick et al. | |
| 7,303,095 B2 * | 12/2007 | Nagelski | A47F 1/087 221/256 |
| 7,395,135 B2 | 7/2008 | Kim | |
| 7,502,664 B2 | 3/2009 | Berg | |
| 7,526,440 B2 | 4/2009 | Walker et al. | |
| 7,641,072 B1 | 1/2010 | Vlastakis et al. | |
| 7,689,316 B1 | 3/2010 | Frederick et al. | |
| 7,783,378 B2 | 8/2010 | Pinney et al. | |
| 7,783,379 B2 | 8/2010 | Beane et al. | |
| 7,805,216 B2 | 9/2010 | Shows et al. | |
| 7,844,363 B1 | 11/2010 | Mehdizadeh | |
| 7,853,355 B1 | 12/2010 | Willemse et al. | |
| 7,860,605 B2 | 12/2010 | Frankel | |
| 8,020,725 B2 | 9/2011 | Yuyama et al. | |
| 8,180,484 B2 | 5/2012 | Baker et al. | |
| 8,190,291 B2 | 5/2012 | Beane et al. | |
| 8,215,520 B2 * | 7/2012 | Miller | A47F 1/126 211/59.2 |
| 8,646,650 B2 * | 2/2014 | Lockwood | A47F 1/126 211/1.51 |
| 8,910,827 B2 * | 12/2014 | Lockwood | A47F 1/126 221/14 |
| 9,171,415 B2 * | 10/2015 | Adams | E05G 1/04 |
| 2001/0000644 A1 | 5/2001 | Lewis et al. | |
| 2002/0173875 A1 * | 11/2002 | Wallace | G06F 19/326 700/242 |
| 2004/0099683 A1 * | 5/2004 | Shows | G06F 19/3462 221/263 |
| 2004/0104241 A1 * | 6/2004 | Broussard | A61J 7/02 221/289 |
| 2004/0108323 A1 | 6/2004 | Shows et al. | |
| 2004/0204954 A1 | 10/2004 | Lacko | |
| 2007/0016327 A1 * | 1/2007 | Yuyama | G07F 9/026 700/231 |
| 2009/0125324 A1 | 5/2009 | Keravich et al. | |
| 2009/0240528 A1 | 9/2009 | Bluth | |
| 2009/0287350 A1 * | 11/2009 | Johnson | G06F 19/3462 700/236 |
| 2010/0010666 A1 | 1/2010 | Adams | |
| 2010/0017296 A1 | 1/2010 | Spignesi et al. | |
| 2010/0030667 A1 * | 2/2010 | Chudy | G06F 19/3462 705/28 |
| 2010/0268380 A1 | 10/2010 | Waugh et al. | |
| 2011/0130873 A1 | 6/2011 | Yepez et al. | |
| 2011/0145073 A1 | 6/2011 | Richman | |
| 2011/0153342 A1 | 6/2011 | Rose | |
| 2012/0310410 A1 | 12/2012 | Adams et al. | |
| 2016/0147977 A1 | 5/2016 | Adams et al. | |
| 2017/0076066 A1 | 3/2017 | Adams et al. | |
| 2019/0066828 A1 | 2/2019 | Adams et al. | |

* cited by examiner

| Date/time | Rx Number | Customer Name | Oxycontin 10mg 55 555-5555-55 Quantity | Inventory | Pharmacist | Pharmacist Initials |
|---|---|---|---|---|---|---|
| 7/7/08 11:00am | 6544321 | Adams, Patrick Address ID # | -30 | 340 | | |
| 7/8/08 10:00am | 6544333 | Walters, Ed Address ID # | -100 | 240 | | |
| 7/8/08 3:00pm | 6544444 | Smith, John Address ID # | -40 | 200 | | |
| 7/9/08 9:00am | inv#12345 | CII 222 # 356645 Address ID # | +300 | 500 | | |
| 7/10/08 4:00pm | 653456 | Jones, Sally Address ID # | -90 | 410 | | |
| 7/10/08 4:00pm | Automation Correction: | Crushed tablets(s) Address ID # | -1 | 409 | | |

FIG. 3a

| Medication | Strength | NDC | Quantity in Back Stock | Quantity in Dispenser | Quantity on Hand |
|---|---|---|---|---|---|
| Oxycontin | 10 mg | 54868-3813-00 | 103 | 340 | 443 |
| | 20 mg | 54868-3814-00 | 54 | 100 | 154 |
| | 40 mg | 54868-3815-00 | 100 | 100 | 200 |
| | 80 mg | 59011-0107-10 | 69 | 220 | 289 |
| Oxycodone | 10 mg | 54868-0346-00 | 40 | 50 | 90 |
| | 20 mg | 54868-0395-00 | 87 | 22 | 109 |

FIG. 3b

SECURE CABINET FOR DISPENSING ITEMS

CROSS-REFERENCE TO RELATED APPLICATIONS

This application is a continuation of U.S. patent application Ser. No. 14/923,949, entitled "Secure Cabinet for Dispensing Items", filed on Oct. 27, 2015, which itself is a continuation of U.S. patent application Ser. No. 13/589,012, entitled "Secure Cabinet for Dispensing Items", filed on Aug. 17, 2012, issued as U.S. Pat. No. 9,171,415 on Oct. 27, 2015, which itself claims priority to and the benefit of the filing of U.S. Provisional Patent Application Ser. No. 61/525,103, entitled "Secure Cabinet for Dispensing Items", filed on Aug. 18, 2011. U.S. patent application Ser. No. 13/589,012 was a continuation-in-part application of U.S. patent application Ser. No. 12/499,043, entitled, "System to Secure, Control, Inventory and Dispense Items", filed on Jul. 7, 2009, now abandoned, which itself claims priority to and the benefit of the filing of U.S. Provisional Patent Application Ser. No. 61/134,034, entitled "PharmaSafe Pharmacy Safe with Time-Delay Automated Counting Technology, Authorization Required Time-Delay Safe Door, Pharmacy Software Interface and Electronic Control Inventory Log for Perpetual Inventory", filed on Jul. 7, 2008, and the specifications and claims thereof, if any, are incorporated herein by reference.

BACKGROUND OF THE INVENTION

Field of the Invention (Technical Field)

Embodiments of the present invention relate to a safe/secure cabinet and system that preferably protects and deters the internal and external threat of theft and robbery, especially useful for controlled and non-controlled pharmaceutical medications and other applications. An embodiment incorporates several technologies to secure, control, electronically inventory and dispense contents of the system.

Description of the Prior Art

Prior art devices store medication inventory in predetermined quantities. Specific individualized doses for a particular patient cannot be delivered. In many small hospitals, medications are dispensed outside the pharmacy and this is usually done with a medication cabinet that can only dispense what is already pre-prepared by the pharmacy.

BRIEF SUMMARY OF THE INVENTION

An embodiment of the present invention relates to a safe for securing and monitoring an inventory of products which includes a product storage area, at least one product dispensing unit, a locking mechanism inhibiting access to products disposed within said safe, and a reporting system which includes a processor executing software stored in a tangible computer-readable medium, the software causing the processor to generate at least one report, and the processor executing the software and maintaining an inventory log of dispensed products and a user's access. The safe can also include an authorization mechanism, which authorization mechanism can optionally require entry of biometric data through one or more biometric data gathering units. The biometric data can include but is not limited to one or more fingerprints, a retinal scan, face recognition, kinetic biometric—a device that a user wears and it recognizes the user's gait, combinations thereof, and the like. The reporting system can continuously maintain an inventory control log, and the log can include information required to comply with a law or with a governmental regulation.

In one embodiment, the reporting system can record one or more of the following: a time when the safe is opened, a time when the safe is closed, a time when a breach in a security feature of the safe occurs, the identity of an individual, and a combination thereof. Optionally, a specific authorization sequence can be required in order to obtain a product stored within the safe. The safe can be compartmentalized into a plurality of areas wherein at least some of the areas are independently lockable. The reporting system can optionally generate a perpetual inventory snapshot. Optionally, the safe can include automated product counting. The safe can also optionally report in real-time.

In one embodiment, the safe can include one or more product back-stock containers. The safe can also optionally include a user-authentication for product dispensing. The safe can further include a user-authentication for product inventory reporting. Optionally, the safe can be caused to dispense a product from an instruction sent from a remote location. Optionally, the safe can be disposed within a nursing area. The safe can also include an adjustable product dispensing time delay. The inventory log can be directly electronically transmittable, and the inventory log can include a perpetual inventory log.

An embodiment of the present invention also relates to a method for dispensing a product and maintaining a product inventory log which method includes providing a safe cabinet, the cabinet capable of storing and dispensing a product; and a computer executing software stored on a tangible computer-readable media wherein the computer maintains an inventory control log for product dispensed from the cabinet and records an identity of a user who accesses the safe cabinet. The computer can cause product to be automatically dispensed from a secure location within the cabinet, which can optionally be in response to data from a prescription being input into the computer. The data can be input into the computer at a location within a same building where the cabinet is disposed, or the data can be input into the computer at a location which is not within a same building wherein the cabinet is disposed. Optionally, the inventory control log can comprise information required by a governmental body which can be required by a governmental regulation. In one embodiment, the cabinet can include a metal enclosure. The software can cause the computer to require an authentication prior to dispensing product. The product dispensed can include a controlled substance. The method can optionally require user authentication prior to dispensing the product.

An embodiment of the present invention also relates to a method for generating an electronic perpetual inventory control log which includes providing a system for dispensing pharmaceutical prescriptions, the system automatically maintaining an electronic perpetual inventory control log. The log can be electronically transmitted to an appropriate governmental body.

Objects, advantages and novel features, and further scope of applicability of the present invention will be set forth in part in the detailed description to follow, taken in conjunction with the accompanying drawings, and in part will become apparent to those skilled in the art upon examination of the following, or can be learned by practice of the invention. The objects and advantages of the invention can be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIGS. 3a and 3b are illustrations of an inventory log and a perpetual inventory report;

DETAILED DESCRIPTION OF THE INVENTION

Figure 1:
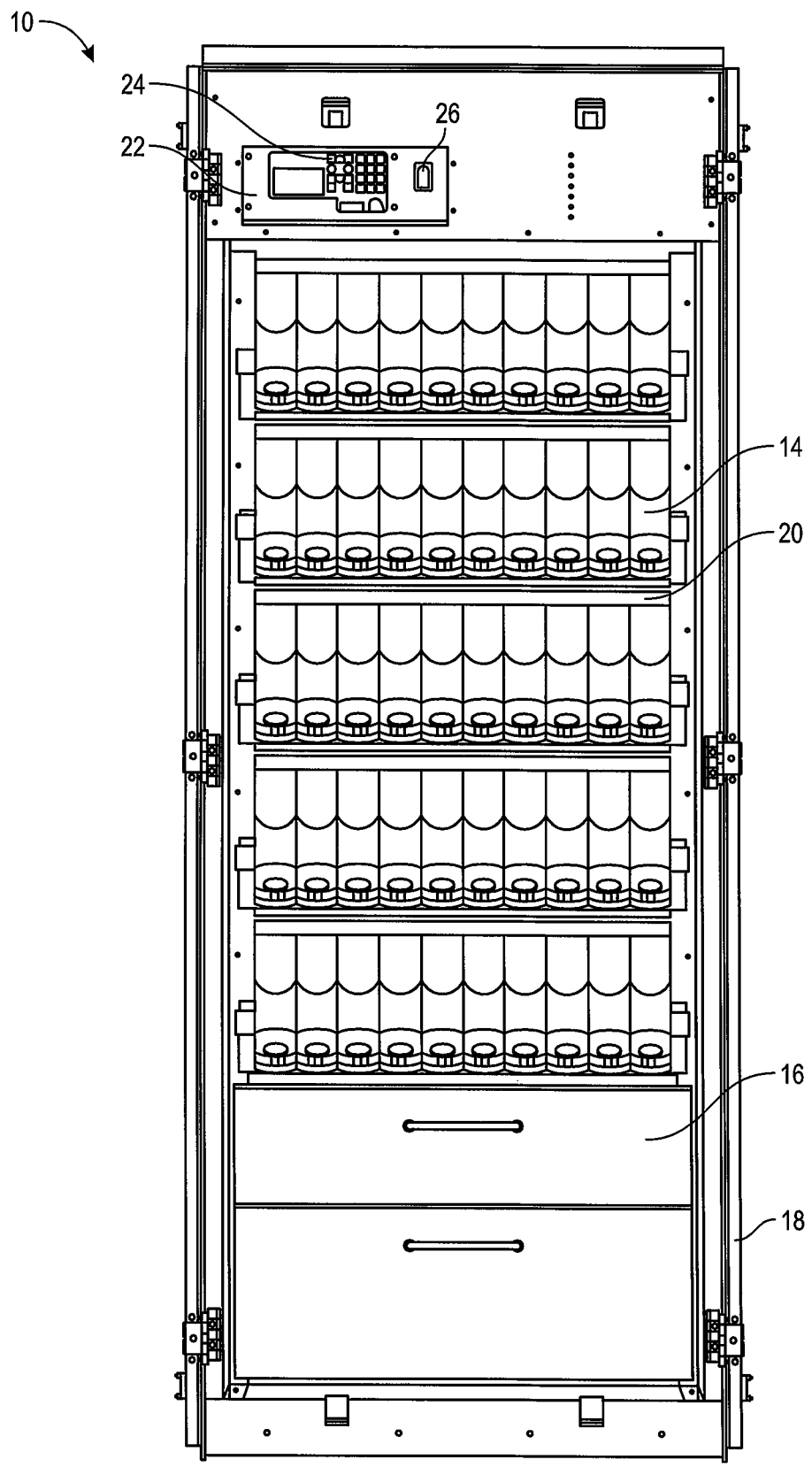
FIG. 1 is an illustration of a front view of an embodiment of the present invention.

Embodiments of the present invention relate to an intelligent safe and/or secure cabinet which can have a plurality of models of various sizes that contain various numbers of dispensers for a specific number of pharmaceutical narcotic/controlled and/or non-controlled medications for security and for inventory control and logging. The invention can also be used for dispensing other items besides medications, including but not limited to firearms, ordinance, chemicals, substances, biological materials, gems, precious metals, etc. The descriptions to pharmaceuticals and medications as set forth herein are for purposes of illustrating one application of the present invention, however, the invention is not limited to pharmaceuticals and medications and can be used for any item requiring control and/or inventory and/or dispensing and/or security.

Embodiments of the present invention reduce and/or prevent access and handling of items thereby reducing the opportunity to divert items. In addition, embodiments of the present invention use dispensing technology to preferably automatically count the items thereby reducing the opportunity for human error. Records and inventory can be kept with regard to each item dispensed. The cabinet comprising the safe can have a time delay on the door and preferably each access is controlled and recorded.

The terms "safe", "kiosk", and/or "cabinet", as used throughout the specification and claims, is intended to include any device, apparatus or structure capable of deterring or otherwise inhibiting, at least partially, access to the contents or items therein by one or more persons. The terms "cabinet", "kiosk", and "safe" are used interchangeably throughout the specification and claims. Throughout the specification and claims the safe, kiosk, and/or cabinet preferably comprises an intelligent device with onboard processing and memory capability. The term "intelligent" as used throughout the specification and claims includes but is not limited to the capacity to acquire and apply knowledge and can thus optionally comprise software.

The terms "product", "item", and/or "contents" as used throughout the specification and claims includes but is not limited to any physical item or substance that can be offered to a market that might satisfy a want or need. In addition, in some embodiments, the terms "medication(s)" or "pharmaceutical(s)" are used interchangeably with the term "product" or "item".

The terms "narcotic" and/or "controlled substance" as used throughout the specification and claims are defined by Federal and State regulations and laws. Controlled substance includes Scheduled I-V medications. The term "pharmaceutical formulation" as used throughout the specification and claims includes but is not limited to the specific form of the narcotic/controlled substance e.g. pills and tablets. The term "prescription" as used throughout the specification and claims includes but is not limited to an order to fill and dispense one or more medications.

FIG. 1 illustrates a front view of an embodiment of the present invention. Cabinet 10 can be a free-standing unit or incorporated into an overall filling system and preferably comprises a cabinet. In this embodiment, cabinet 10 preferably includes: frame 12 (see FIG. 4) that preferably structurally holds dispensers 14, bottom drawers 16, hinged doors 18, and dispenser securing mechanism 20. In one embodiment, locking control mechanism 22 is controlled by keypad 24 which can activate alarm 26. Cabinet 10 prevents access to medications and/or items by persons unless authorized by locking control mechanism 22. Locking control mechanism 22 can be electronic or manual and can have specific authorization requirements for entry. Locking control mechanism 22 can record times of opening, closing and any breaches. Each user can have a specific authorization sequence to gain access so that his/her specific code is recorded on a log. Cabinet 10 preferably comprises a stand alone unit that can be manually operated or connected to dispensing software for dispensing. Locking control mechanism 22 and keypad 24 preferably limit access to the safe by an individual, (e.g. controlled substances dispensing software) preferably time controlled and recorded. Locking control mechanism 22 and keypad 24 optionally gather and/or provide information to access cabinet 10. Locking control mechanism 22 optionally allows one or more time delays for dispensing and/or opening cabinet 10 and can be set by each pharmacy based on its particular needs or can be preset. In another embodiment, one or more delays can be introduced in another system, optionally via software.

Cabinet 10 is optionally made from various materials including steel, aluminum, titanium, a composite, plastic material, or any combination thereof, that prevents compromise for gaining entry into cabinet 10. Locking control mechanism 22 can vary according to application and can operate mechanically, digitally or by any means that resists or otherwise inhibits the ability of a non-authorized individual to gain access to cabinet 10 and can optionally include, but is not limited to keypad 24. Dimensions of cabinet 10 can be virtually any size and shape depending on the number of dispensers 14, or containment mechanisms including but not limited drawers, shelves, combinations thereof, and the like, as well as the application to a specific area of the industry. The interior of the safe can be compartmentalized so each specific area can be lockable. Alternatively, larger sections can be lockable, while some areas allow ease of access, or any combination thereof. Access to each locked portion of cabinet 10 optionally requires the authorized user specific code and can be illustrated on the access log. Forced entry or any perceived unauthorized dispensing of product can set off any number of alarms and checks thus initiating a chain of events to secure the contents of cabinet 10 or alert appropriate persons to prevent entry and thus prevent losses from cabinet 10. Entry to any embodiment can require one or more criteria, including, by way of a non-limiting example only, authorized users can use an electronic or manual code, Dulles key, electronic card, biometrics, a touch pad, any other system, apparatus, or method capable of enabling a user to identify themselves individually or as a group, which can be on cabinet 10, or remote from cabinet 10, any combination of entry modes, that is given to the authorized party that gives him/her a unique entry into the safe, combinations thereof, and the like. The alarms can be silent or can be audible and/or visual. Any breach can send electronic signals to appropriate authorities, representatives of a company, or any remote or on-site safety system. Perpetual inventory can be kept within the software contained in the safe, or remote from the safe.

Embodiments of the present invention can integrate pharmaceutical dispensing technology known in the industry with the locking depository safe and/or cabinet, inventory management software and reporting system providing a user ready product for counting, dispensing, tracking and reporting on controlled products. An embodiment of the present invention solves the problem of simultaneously physically securing, processing and quantity tracking of an item and providing the reports required by government agencies and management.

Figure 2:
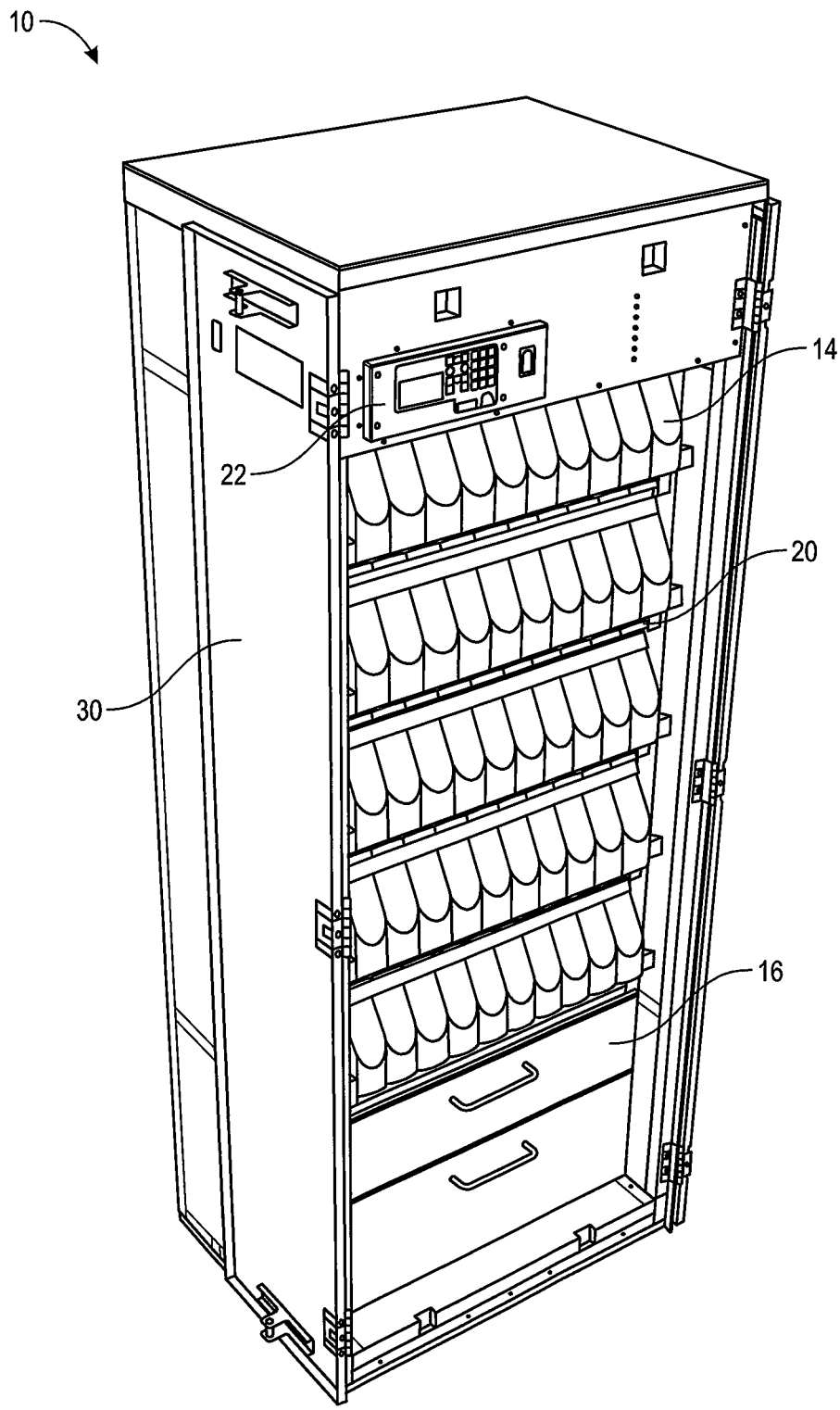
FIG. 2 is an illustration of a perspective view of the FIG. 1 embodiment.
Figure 4:
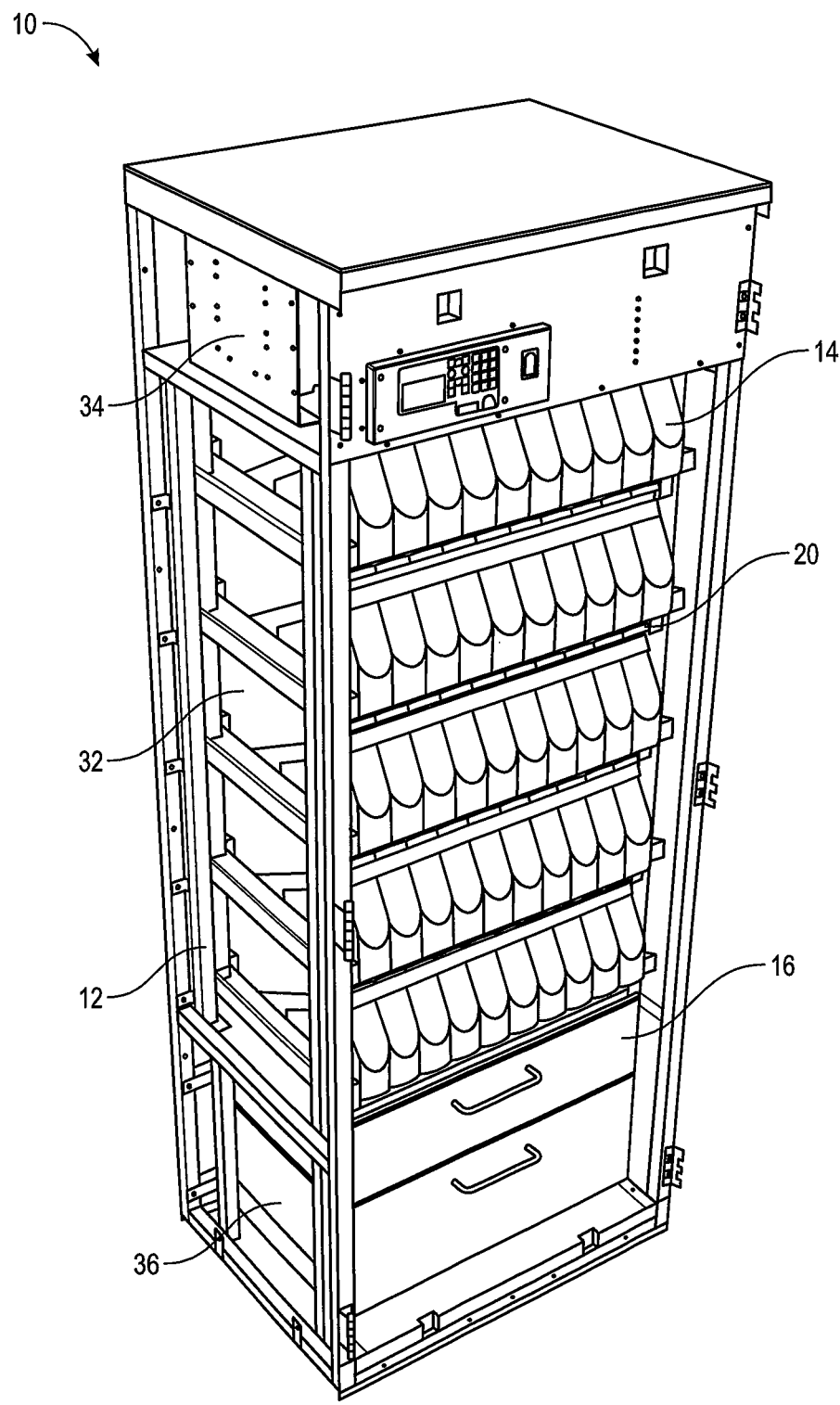
FIG. 4 is an illustration of a perspective view of the FIG. 1 embodiment with the side panel removed.

FIG. 2 illustrates a perspective view of cabinet 10 with dispensers 14 as individual housing units within cabinet 10 capable of holding a pharmaceutical formulation. Cabinet 10 preferably comprises locking door 30 and drawers 16. An embodiment contains electronic counting technology for pharmaceutical pills, tablets or any other medication or item that requires or otherwise benefits from security. The exact count of medications for each prescription or medication order can be counted out by automated counting technology. Items can be dispensed immediately or delayed for a specified time. A delay can alternatively be provided between subsequent dispensals of items. Ranges of delay include but are not limited to between approximately one minute to approximately 24 hours; between approximately one minute and approximately 15 minutes; and between approximately 30 seconds to approximately five minutes. The amount of delay time can be set by an authorized agent. An authorized agent is preferably set by an officer or other designee of the company with authority to access the cabinet. In one embodiment, locking control mechanism 22 cannot be changed by any other persons unless the authorized agent gives such authority. Each change to the specified time can optionally be on an electronic log along with the authorized agent name or mark. Software for the preferred embodiment retains these changes in the electronic log and reporting system. The counting technology can be specifically made for an embodiment of the present invention. The counting technology can be manual or electronic. Counting technology can deliver any types of dosage forms and containers including but not limited to pills, capsules, crèmes, liquids, vials, tubes, ovals, bottles, pre-filled syringes, ampules or other items. Dispensers 14 preferably deliver or allow access to one or each of these dosage forms. Cabinet 10 can optionally secure a plurality of medications in a shelving system while preventing access to a selected medication using locking control mechanism 22 while generally limiting access to all medications. For example, dispenser 14 can preferably dispense an exact count or can supply a stock bottle that is poured from a manually counted prescription while the remainder of the medication is returned to bottom drawer 16 where it is again securely locked until the next authorized usage. FIG. 4 illustrates the FIG. 1 embodiment with side panel removed to illustrate shelving units 32, control board 34 and interior drawers 36. Embodiments of the present invention can preferably provide a configurable time delay from when a prescription is received until the apparatus starts counting the medications to fill the prescription or between subsequent doses of a medication.

Embodiments of the present invention increase security by ensuring that the appropriate time delay configuration is set so that it cannot be easily changed during daily or routine use of the cabinet. A preferred embodiment integrates into virtually any existing pharmacy and/or automated system.

Embodiments of the present invention can have compartments for back stock inventory to insure all product is secure. FIG. 3a is an illustration of an inventory control log report, and FIG. 3b is an illustration of a perpetual inventory. The inventory control log reports, and the like allow for any real-time reporting of activity with use of the cabinet. Perpetual inventory reports preferably present a running accounting of inventory, including back stock and can be generated for time specific intervals. A preferred embodiment comprises the creation, tracking and reporting functionality. A preferred embodiment can inhibit and/or prohibit unauthorized access, adhere to time delays as appropriate, track the quantity and movement of inventory and provide accountability to individual persons for the management of the inventory and reporting. A preferred embodiment provides an electronic perpetual inventory control report which can be delivered electronically.

An embodiment of the present invention comprises reporting and functionality including but not limited to: providing a CII Inventory Control Log and perpetual inventory snapshot report; providing a CIII through CV Inventory Control Log and perpetual inventory snapshot report; correction to perpetual inventory in the case of a miscount, or other problem; time-release dispense; and locking mechanism integration. Embodiments of the present invention comprising software preferably provide user authentication, inventory tracking, control of counting automation and reporting. Embodiments comprise software integration, wherein users preferably can be required to authenticate their identity to open the apparatus or otherwise dispense product and separately authenticate to the software for tracking.

Some embodiments of the present invention are optionally capable of dispensing product at night and/or from an instruction from remote location. Embodiments of the present invention fill a need for not only night dispensing but remote dispensing. As a non-limiting example, in a hospital setting, an embodiment of the present invention is optionally connected to a pharmacy system but placed in a nursing area not located within the pharmacy. When there is a pharmaceutical order into the pharmacy, the pharmacist can make the dose available at the remote location of the present invention.

An embodiment can comprise the required inventory management developed within the software system in an integrated manner (described as an "integrated approach") and/or it can be developed as a separate, standalone software package that interfaces with an embodiment of the present invention (described as an "interfaced approach").

Embodiments comprising an integrated approach preferably provide perpetual inventory of the dispensers and/or other containment mechanisms provide back stock storage which is then preferably updated and reported by the software. Embodiments comprising an interfaced approach preferably comprise a separate, standalone software module. Embodiments with this module comprise the ability to keep track of the back stock in the cabinet and communicate with the preferred software to get the current inventory of the dispensers. Operationally this can be done through a defined transactional interface or through any appropriate connection directly to the apparatus database. A reporting mechanism can optionally be part of the separate module.

Figure 5:
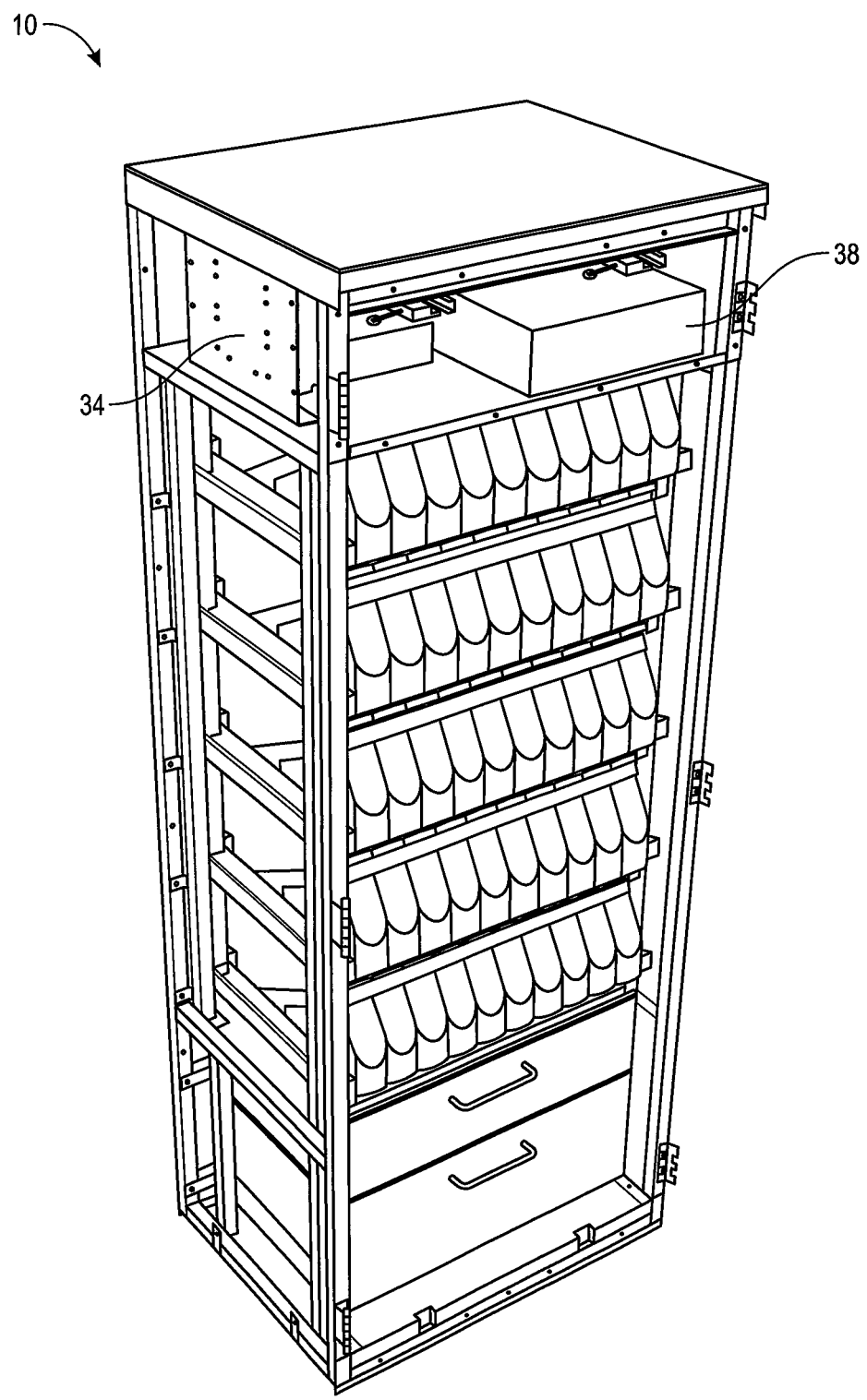
FIG. 5 is an illustration of a perspective view of the FIG. 1 embodiment with the side and front top panel removed.
Figure 6:
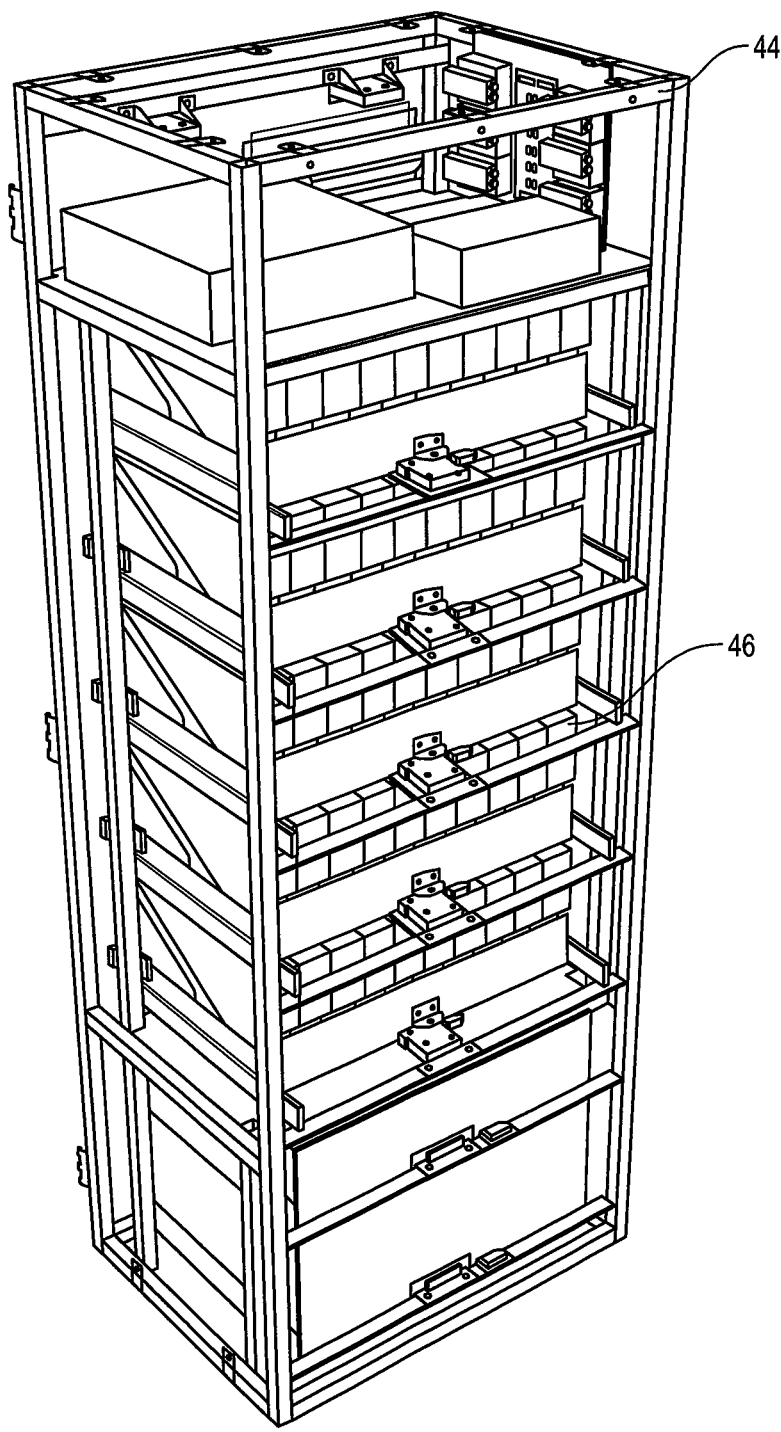
FIG. 6 is an illustration of a perspective view of the FIG. 1 embodiment with the side and front top panel removed and illustrating the interior of the cabinet.

FIGS. 5 and 6 illustrate the "brain" components of the preferred embodiment of the present invention, including central processing unit 38 (see FIG. 5). Cabinet 10 can optionally have time delay mechanisms for safe opening and medication dispensing that can be set for the user's specific needs. In one embodiment, time-delay mechanisms can only be set and reset by authorized agents. In this embodiment, only authorized agents can have access codes to open the safe or dispense items. Authorized agents and level of access can optionally be set by someone with authority, such as an owner or officer of the company that owns cabinet 10. All access and dispensing of the contents of cabinet 10 can produce an electronic log that illustrates a plurality of identifiers including but not limited to date, time, item type, quantity and the person that is accessing the safe or dispensing items. Time delay mechanisms can optionally be manual or electronic and are designed so changes cannot be made by a user to circumvent the delay default prescribed by the authorized authority. Specific time can optionally be set from no time delay, or set to some finite delay. The clock for time delay can be included in an embodiment or disposed at a remote location that communicates with the safe electronically. In one embodiment, all time delay changes can be reported electronically to persons the purchaser deems appropriate. Optionally, log reports can be generated for virtually any pertinent information. FIG. 6 illustrates an embodiment of the shelving mechanism as well as a back portion of dispensers 46.

Cabinet 10 optionally can allow an authorized user to enter a number and scan the items associated with an invoice. Embodiments of the present invention can preferably log the events for reporting and can update the inventory quantity of the correlated back stock.

Embodiments of the present invention preferably comprise software that has a replenishment tracking and control function. Embodiments of the present invention optionally comprise the ability to change a replenishment function, to meet the needs of scheduled inventory replenishments, or increase in need, as non-limiting examples. As a non-limiting example, as the stock bottles are scanned, the resulting events are made available to the inventory control reports including but not limited to back stock inventory, and the person causing the product to be dispensed. Preferably following replenishment, any adjustments can include a logged explanation and remaining stock and/or is preferably scanned back into cabinet 10 and the back stock inventory levels are updated.

In one embodiment, when an item is received and dispensed over an interface and/or entered directly into software in the embodiment, the counting and dispensing of the item is not launched until a configured period of time has expired. Embodiments with the inventory count-out capability and/or any other operation that causes product to go from hopper to buffer (e.g. dispenser maintenance) is also subject to the configured time delay.

Embodiments of the present invention comprise an interface module that preferably communicates with cabinet 10. Communication between the software allows cabinet 10 to preferably let internal software know who has authenticated and what containment mechanisms can be accessed. Data transmitted from cabinet 10 to software can include but is not limited to user authentications, safe-open, safe-close (which can optionally include a drawer or container number), and/or user-created information, user-removed information (to keep user databases in sync).

Embodiments comprising software optionally allow remote capabilities for locking and unlocking cabinet 10. Embodiments comprising software can preferably write reports for inventory control log and/or the perpetual inventory snapshot.

Embodiments comprising an interface approach preferably communicate with an inventory management system. This communication is used for embodiments that need additional data for remote transmission of e.g. controlled medications. The following are non-limiting operational scenarios identified for clarification of the present invention:

Prescriptions are preferably entered in an embodiment of the present invention with the appropriate software. After transmission over an interface, in a standalone environment, the prescription can be accepted by the software if the medication is either in the dispenser or in the cabinet's back stock inventory. Optionally, embodiments can accept any prescription transmitted. Once a prescription is identified and/or cleared and after an appropriate delay interval as expired, the prescription can be processed. If an embodiment is assigned to a dispenser, the count is launched in the dispenser(s). If an embodiment is not assigned to a dispenser (e.g. the prescription is a manual fill) it is alternatively placed into a scheduled state and is available for manual filling. The time/date of the count launch is preferably recorded for reporting purposes since the buffer area of the dispenser is optionally not within the secure area.

When a vial label of an auto-counted prescription is scanned into the software of a preferred embodiment, the dispenser is activated and the pills are released into the vial.

Software preferably decrements the inventory of the dispenser while quantity filled of the prescription is incremented by the same amount. When the vial label of a manual prescription is scanned or otherwise entered, the user preferably opens the cabinet, which can optionally be after a time delay, retrieves the stock bottle, scans it and counts the manual fill. The scan in this case serves a plurality of purposes. One is to verify that the proper stock bottle has been selected and another is to create a log entry that the stock bottle was removed from the safe. When a user completes the manual counting and selects an appropriate identifier on the manual fill form, the inventory is decremented and the quantity filled of the vial is incremented. Embodiments of the present invention can require the user to count the pills remaining in the stock bottle and enter the quantity before continuing. Embodiments of cabinet 10 preferably transmit transactions when it is opened and then closed.

Alternatively, during replenishment, a user can open cabinet 10 and scan the stock bottle used to perform the replenishment. This optional scan preferably allows identification of the product being replenished and the dispensers and creates a log entry that the product was removed from the cabinet. At the end of the replenishment, if an inventory adjustment is requested, a user can preferably select a predefined reason or type in a free-form field a reason in order to finalize the log. When new stock of controlled substances is received into the pharmacy, the user preferably increments the inventory in the software to reflect the new quantity. Alternatively, a user can scan the barcode on the stock bottle. If appropriate, embodiments of the present invention can prompt the user to enter the required control number. Embodiments of the present invention preferably comprise appropriate range and format checking of control numbers for quality control. Once stock bottles are scanned the back stock inventory is preferably increased accordingly. Preferred software enters appropriate information to the log and is optionally available for reporting. In one embodiment, during replenishment, if cabinet 10, or some secure portion thereof is not properly closed within a predetermined time, an alarm can optionally be activated.

A preferred embodiment allows a user to select at least one of the plurality of Controlled Substance reports or have the reports automatically printed on a predefined schedule. Preferably an inventory control log report is a chronological list of inventory events for each stocked product. This can be provided to the Drug Enforcement Administration ("DEA") as documentation of everything that is being dispensed and acquired in real time. Preferably the report is to be printed and/or saved to an electronic file. Embodiments of the present invention allow for software scanning of acquired medications from the wholesaler into back stock. Medications from a wholesaler must correlate with a specific invoice number and ordering control number as issued by the DEA. Users receiving the medications preferably enter an invoice number and a form control number into the preferred embodiment's software. Quantities are preferably added to the total inventory as back stock. All of the events preferably cause records to be created in the logs. Embodiments with the preferred software also preferably require scanning to take inventory out of back stock before it is used to replenish a dispenser. After a prescription is dispensed, the appropriate quantity can be subtracted from inventory. Preferably reports to correlate to inventory control are a chronological accounting of input and outflow of inventory in real time. Alternatively, time delay or back stock reporting can be performed. Preferably, reporting is similar to reports well known in the industry to preferably provide ease of technology and information transfer. Specific labeling is preferably correlated to back stock scanned and placed into the dispensers.

An embodiment employs an electronic inventory control for the monitoring and accounting of medications dispensed. Reports for pharmaceutical controlled substances/controlled substances in the holding area of the safe as well as the medications contained in dispensers of the unit preferably conform to the federal requirements. Reports can be generated, including by way of a non-limiting example, the following information: 1) acquired medications including invoice numbers, quantity acquired from the wholesaler and CII control number from the DEA222 form; and 2) dispensed medications including the name of the recipient, medication, quantity of dispense, prescription number and initials of person(s) initiating the release of the prescription from the unit. These reports can satisfy federal and state requirements for perpetual inventory tracking. Inventory discrepancies can be identified and/or accessed at the location of the apparatus or can be transmitted. Use of software to preferably account for the inventory at virtually any moment and illustrates all acquired medications by date, wholesaler and invoice number as well as the person receiving said order and can account for deficits to inventory for virtually any reason, and/or any other appropriate recordation useful to the industry. All transactions can be identified in any preferred order including but not limited to chronological order. Chronological order preferably illustrates documentation as to the party receiving the medications or reason for loss. Information stored on the software can be preferably accessed and cross referenced by date, medication, person or party receiving medications, location of medication acquisition, overages, losses and any other pertinent information to comprise a comprehensive reporting system.

Embodiments of the present invention include but are not limited to software that can interface with various existing pharmacy software systems to allow for the (a) automatic filling and dispensing of the narcotic/controlled substance or non-controlled medications from the safe upon "input" of data into the pharmacy system; and (b) integration of the electronic perpetual inventory system and reports. Cabinet 10 preferably has connectivity capability to communicate with external applications to allow a user to authenticate. User credentials are optionally transmitted to external software. Optionally, a user can authenticate to both cabinet 10 and to external software simultaneously.

Alternative embodiments include but are not limited to virtually any software or software communication method as needed, and/or any combination thereof.

Figure 7:
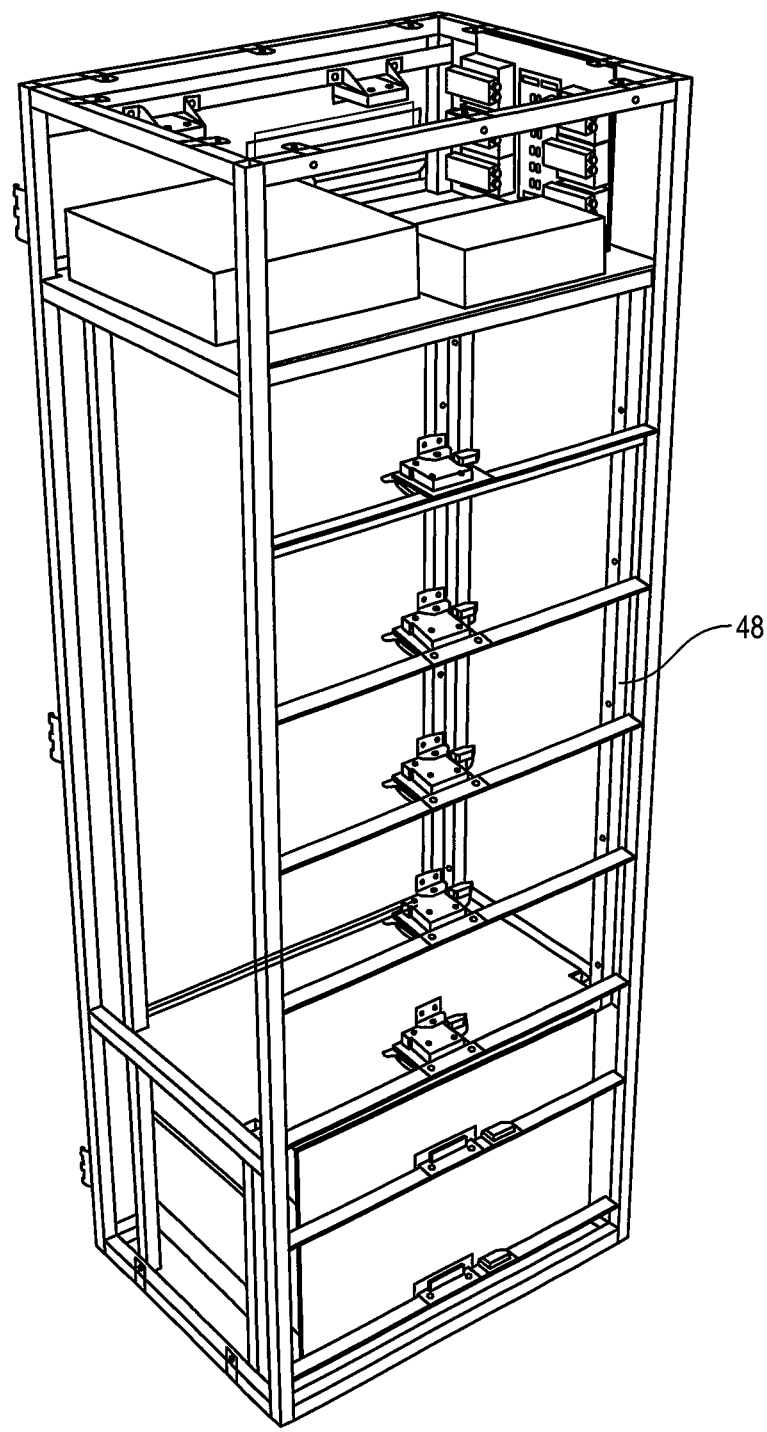
FIG. 7 is an illustration of a front view of a frame according to an embodiment of the present invention.
Figure 8:
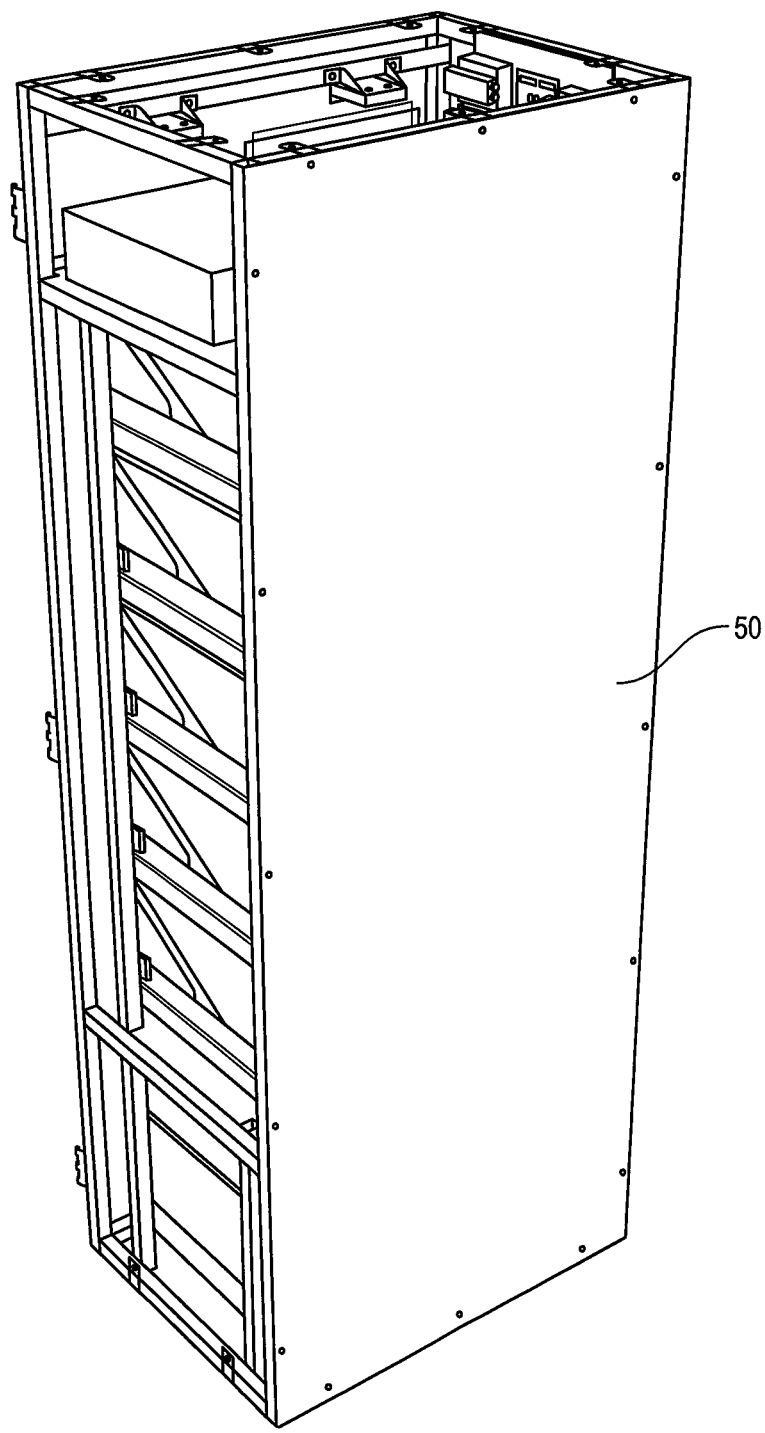
FIG. 8 is an illustration of a back view of an embodiment of the present invention with side panel removed.
Figure 9:
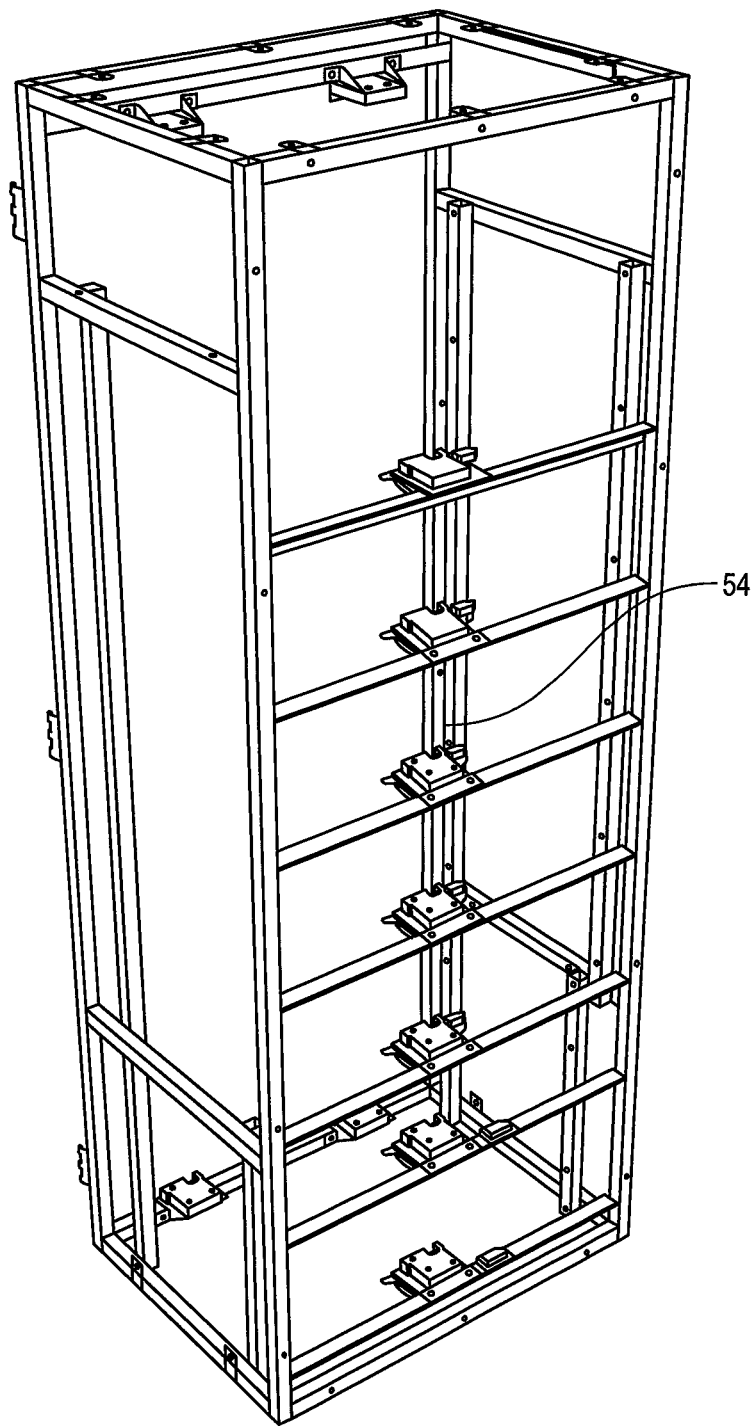
FIG. 9 is an illustration of a front view of a frame according to an embodiment of the present invention.
Figure 10:
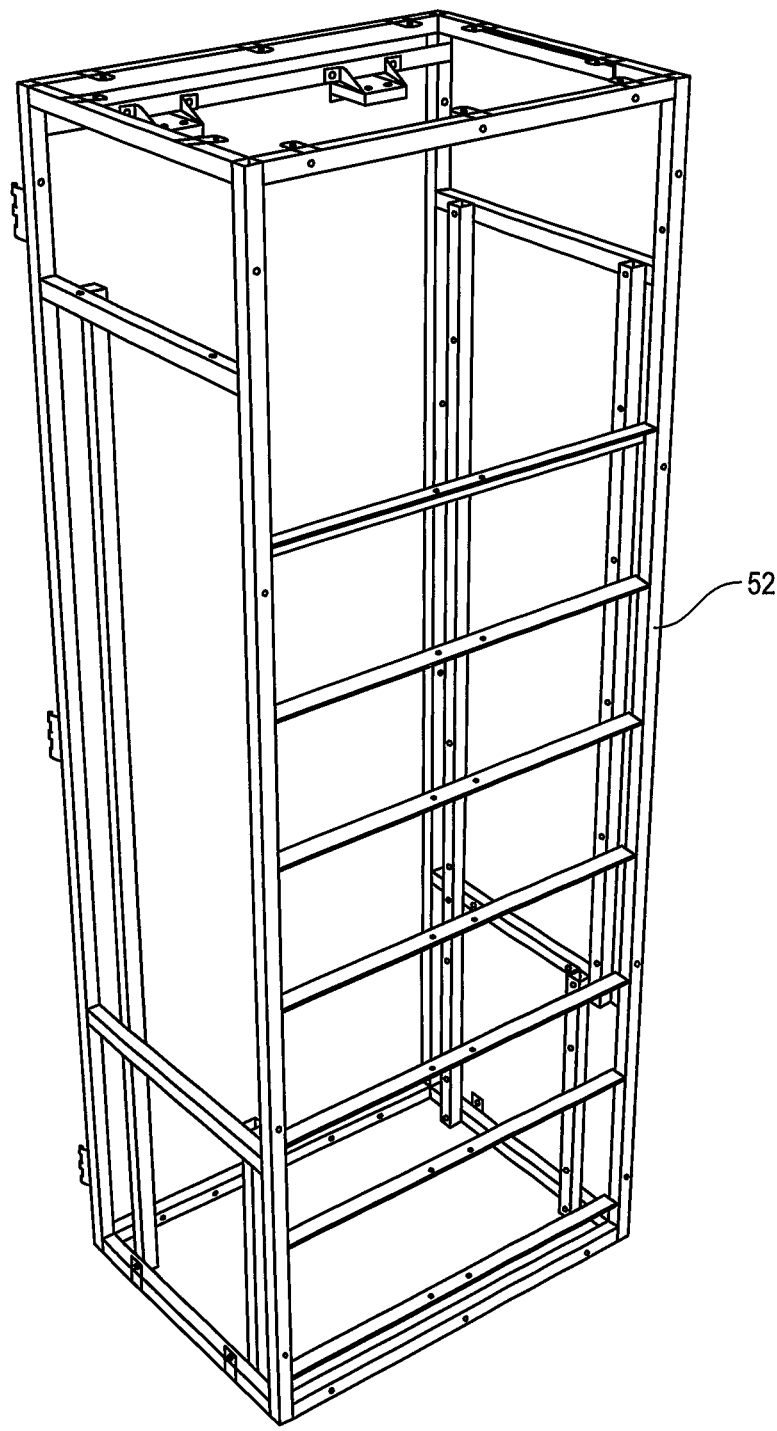
FIG. 10 is an illustration of a front view of a completely bare frame according to an embodiment of the present invention.
Figure 11:
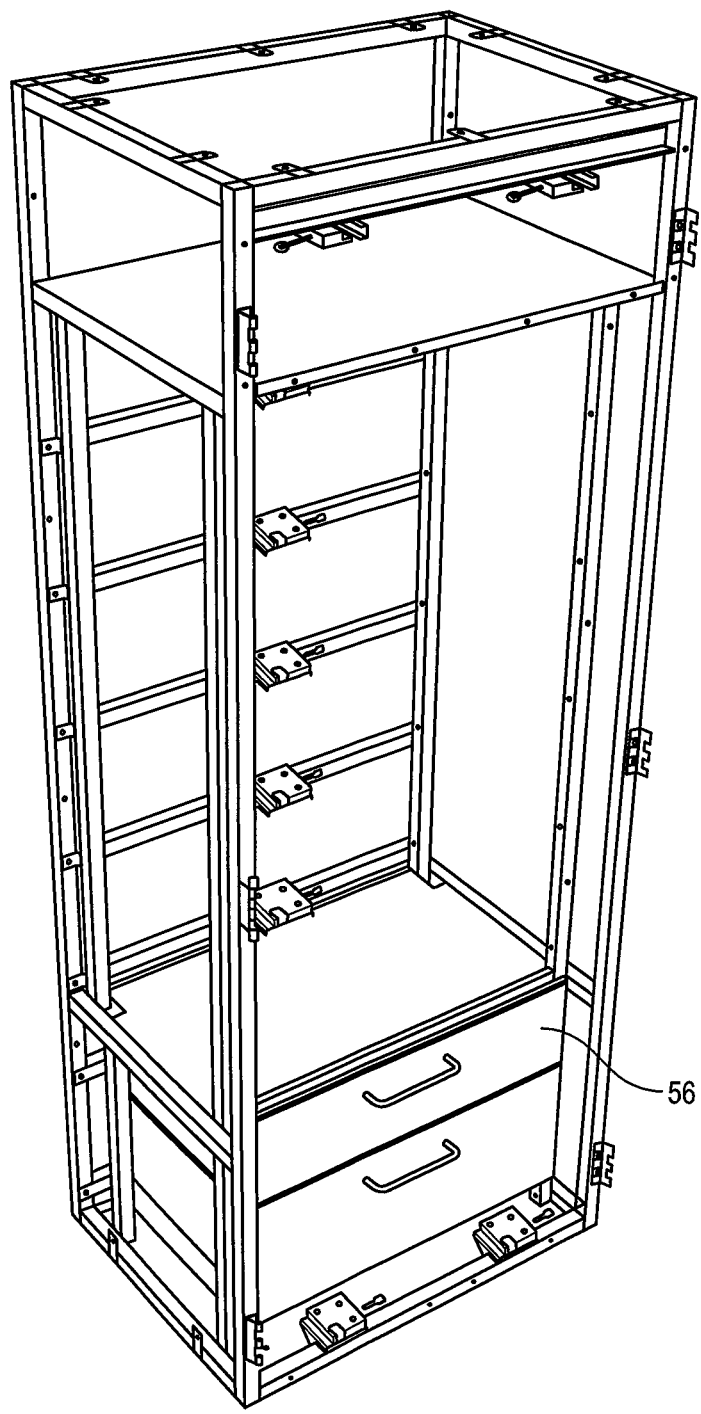
FIG. 11 is an illustration of a front view of a frame according to an embodiment of the present invention with a top shelf and bottom drawers.
Figure 12:
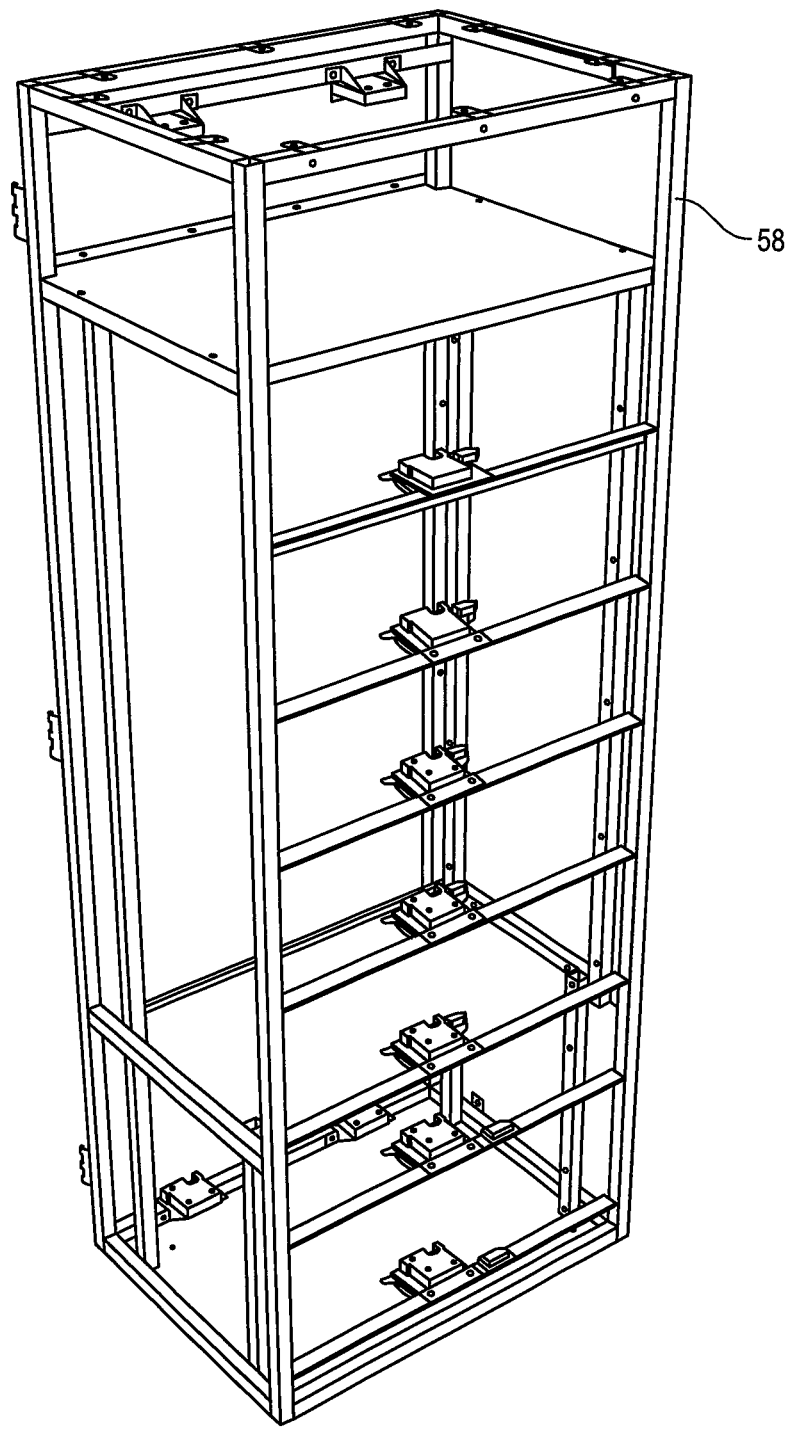
FIG. 12 is an illustration of a perspective view of an embodiment of the present invention.
Figure 13:
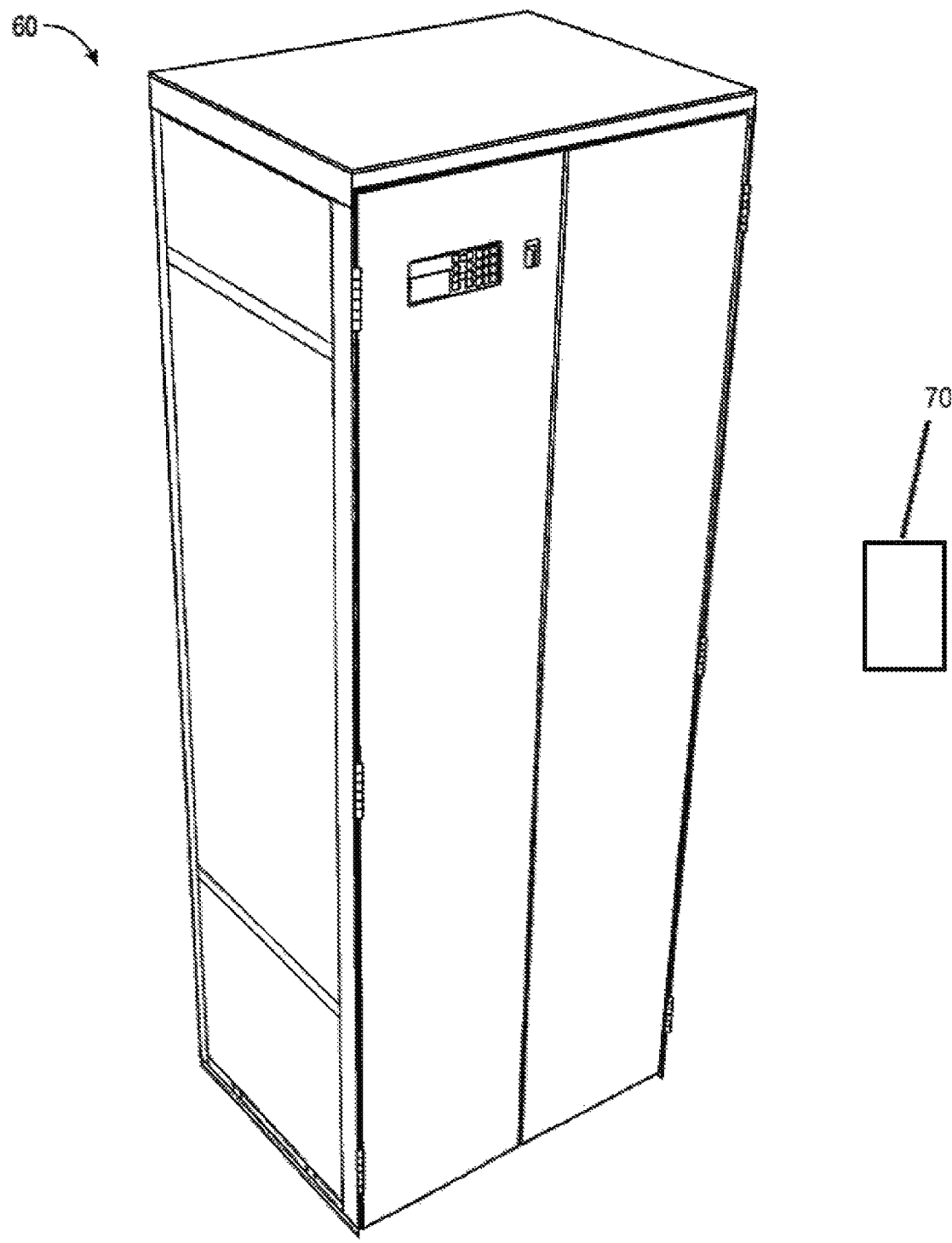
FIG. 13 is a front view drawing illustrating a closed cabinet according to an embodiment of the present invention.

FIGS. 7-13 illustrate components and embodiments of the present invention. FIGS. 7 and 10 illustrate frame 48 and 52 respectively. FIG. 8 illustrates a back panel 50 with a top panel removed. FIG. 9 illustrates shelf locking unit 54. FIG. 11 illustrates a perspective view of an embodiment with bottom drawer 56. FIG. 12 illustrates an embodiment of the present invention with frame 58 for an all dispenser shelving unit. FIG. 13 illustrates a closed and locked embodiment of cabinet 60.

Figure 14:
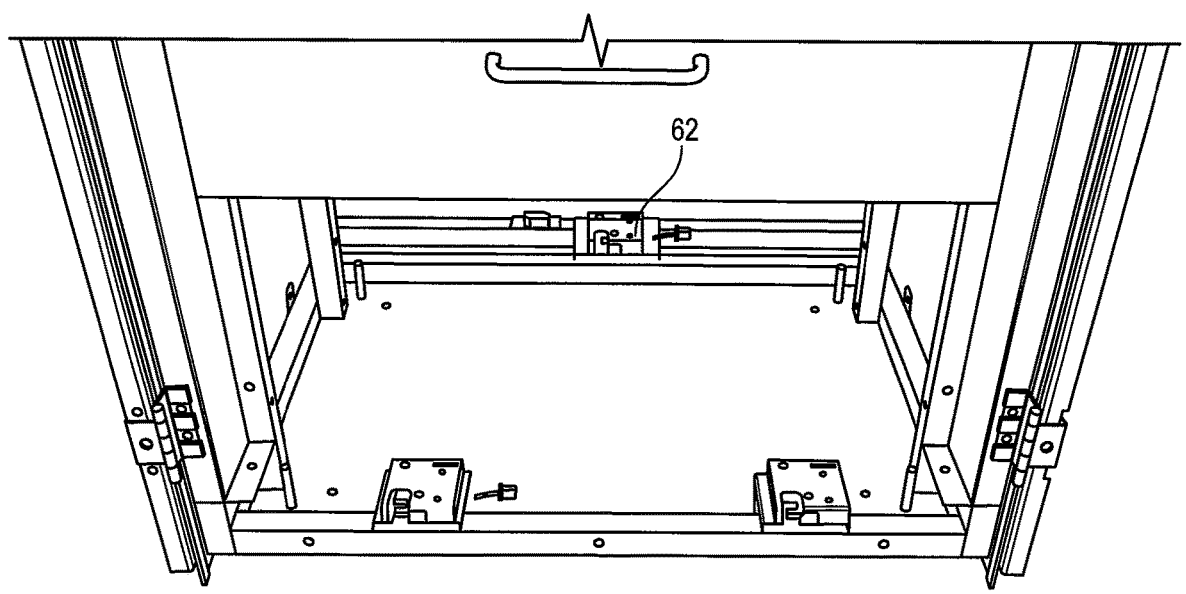
FIG. 14 is an illustration of a close up front view of a bottom drawer opening.
Figure 15:
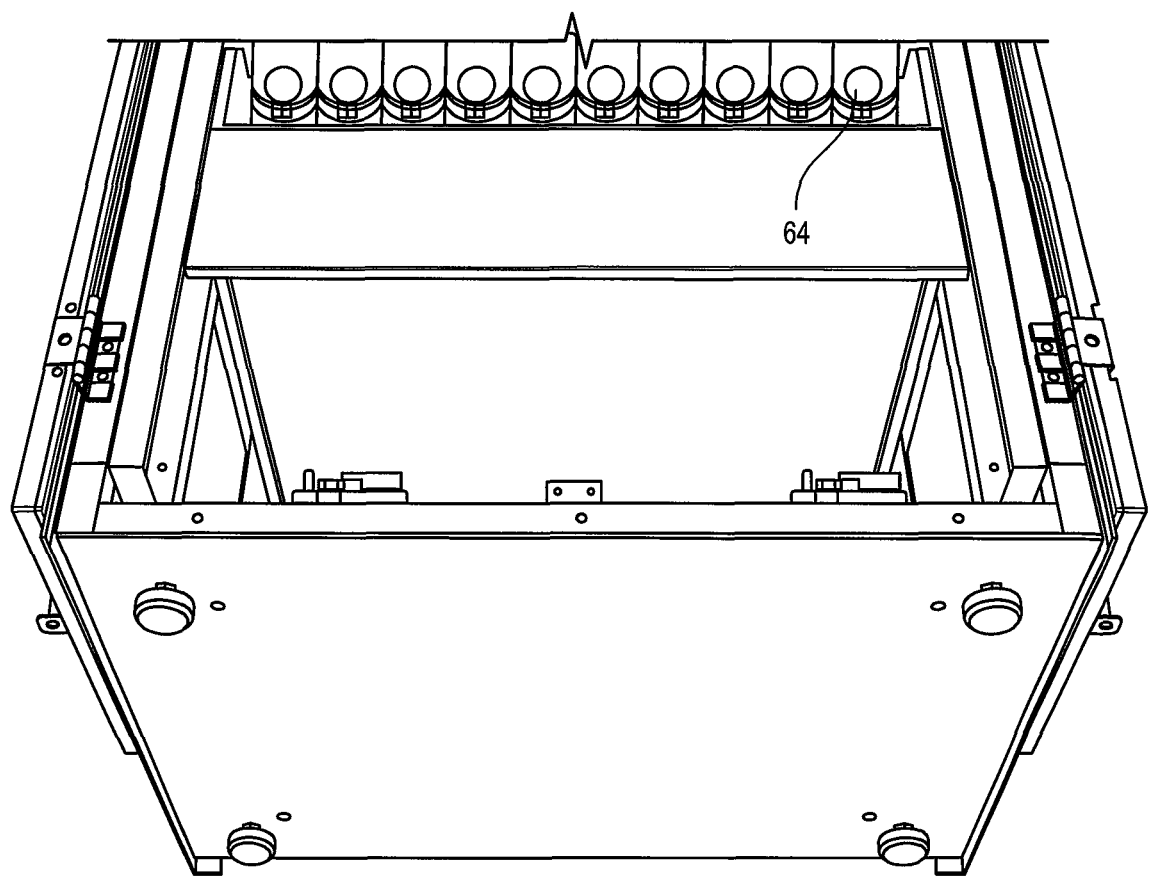
FIG. 15 is an illustration of a close up bottom view of a drawer opening.
Figure 16:
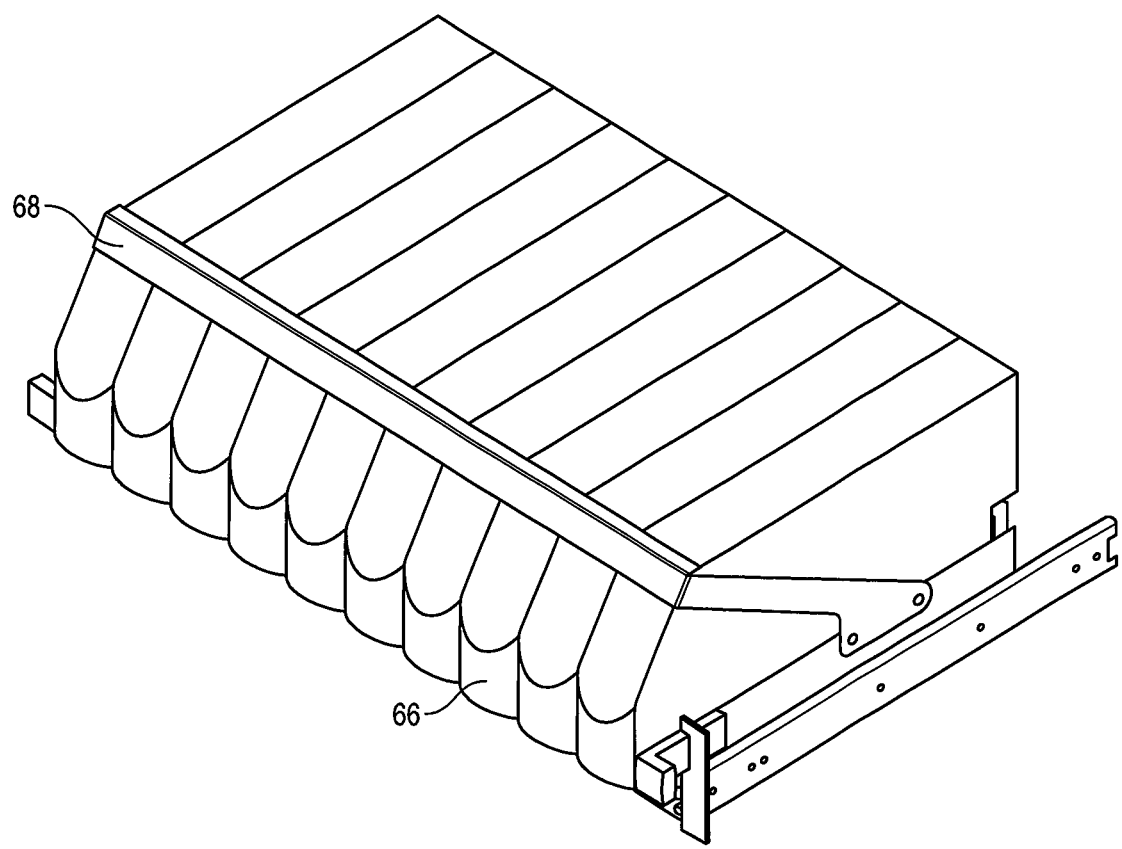
FIG. 16 is an illustration of a dispenser according to an embodiment of the present invention.

FIGS. 14 through 16 illustrate different, close up views of components of different embodiments of the present invention. FIG. 14 illustrates bottom drawer lock 62; FIG. 15 illustrates a bottom view of dispenser door 64; and FIG. 16 illustrates dispensers 66 and dispenser securing mechanism 68.

Figure 17:
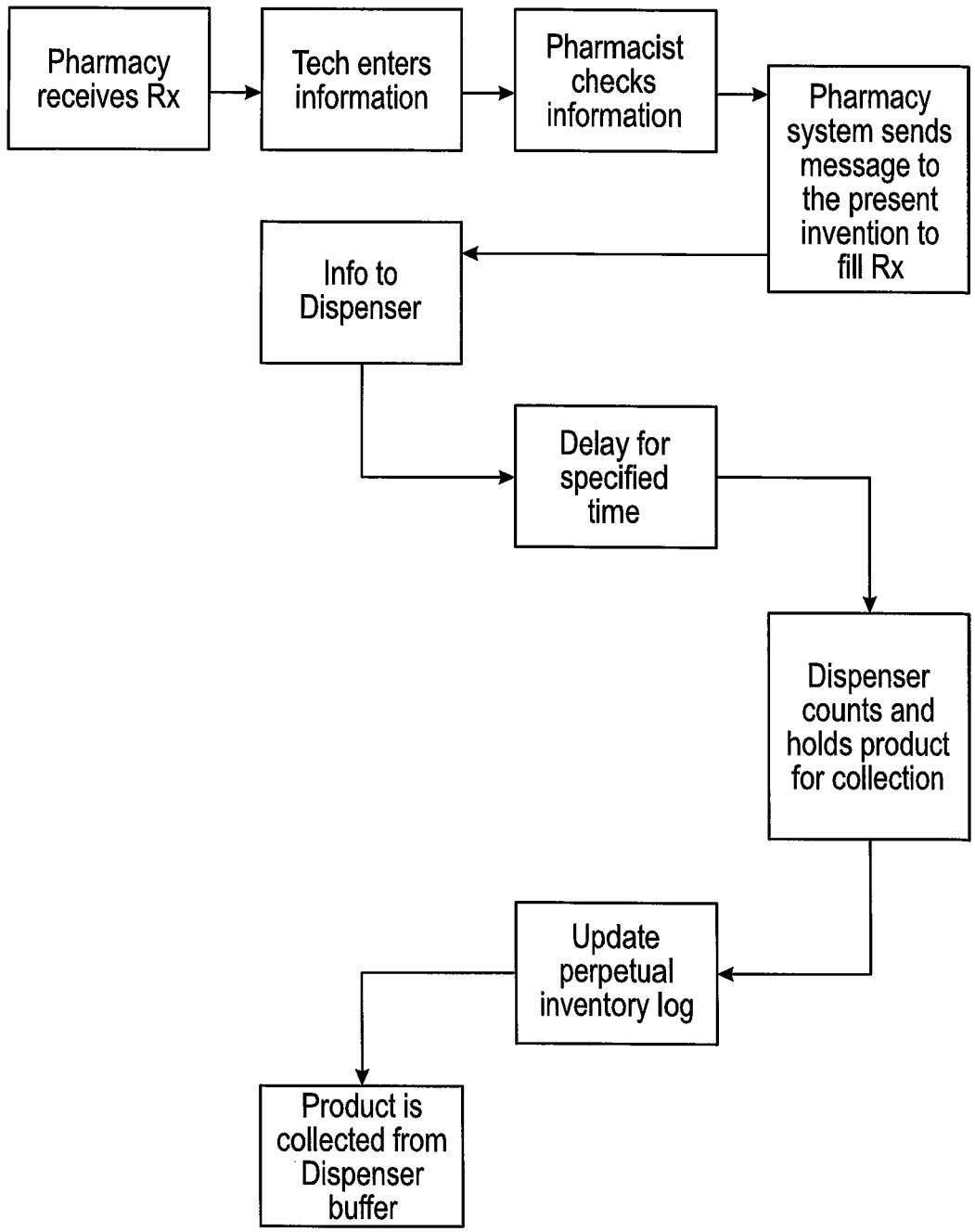
FIG. 17 is a flow chart which illustrates some steps which can occur when a prescription is filled and dispensed.
Figure 18:
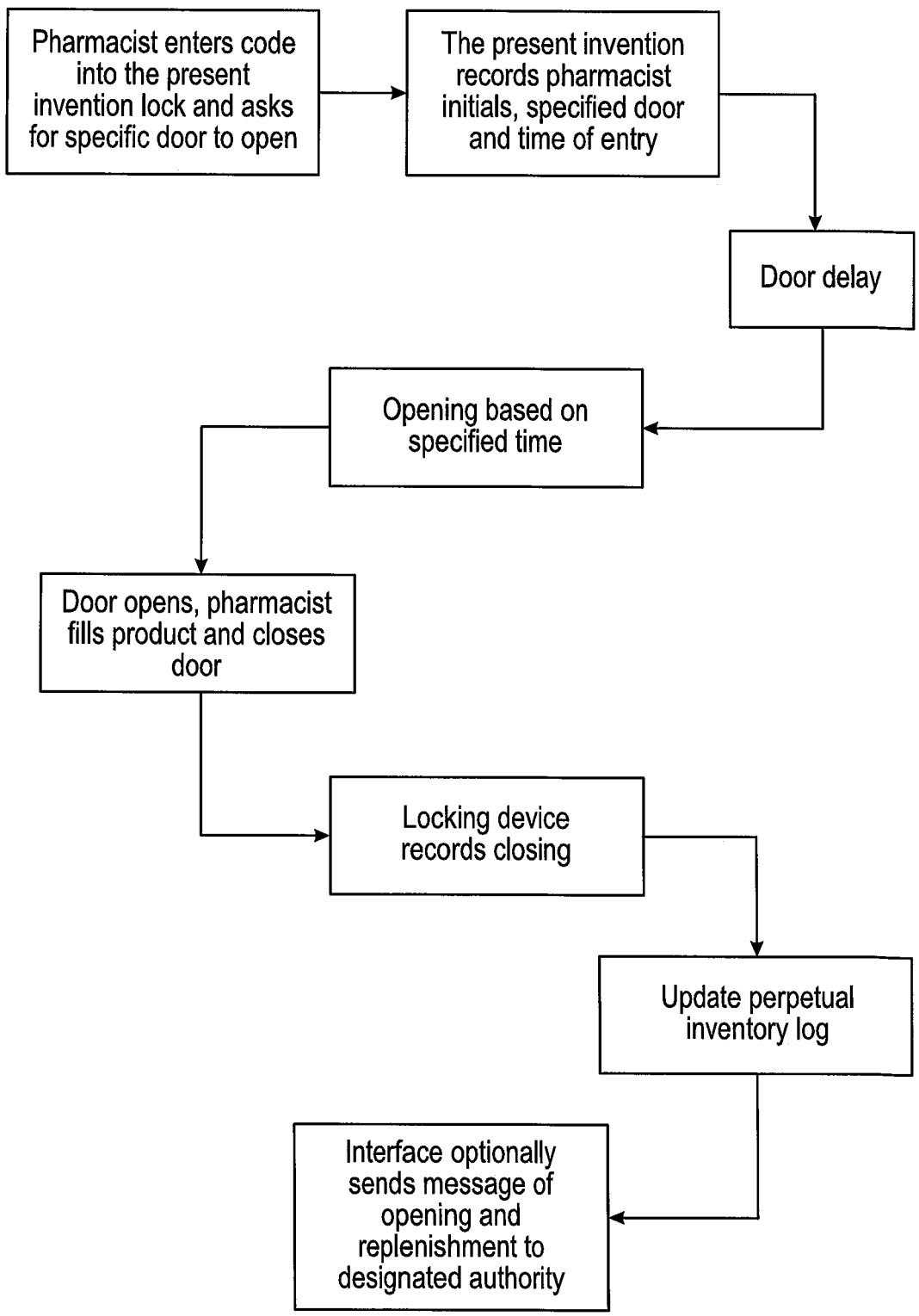
FIG. 18 is a flow chart which illustrates some steps which can occur when a pharmacy's inventory is replenished.

FIGS. 17 and 18 respectively illustrate flow charts according to embodiments of the present invention wherein a prescription is placed and filled, and wherein inventory for a pharmacy is replenished.

Kiosk

One embodiment of the present invention comprises a kiosk that preferably vends various types of over the counter pharmacy and personal health products that tend to be high theft, have an age limitation or must be verified to prevent usage for narcotics manufacturing. FIGS. 24-29 illustrate various embodiments of kiosks. The kiosk preferably uses spiral vending trays controlled by a customer driven touch screen point of sale. A controller is preferably housed in the safe that provides the operational interface. The kiosk preferably maximizes off the shelf components and maximizes SKU count/qty of the customer provided product list. The point of sale system can also integrate with store sales systems and the NPLEX verification system for some Tier 1 type products (see below).

Over the counter medications can be categorized into different tiers. For example, a Tier 3 product is a product that anyone can buy over the counter. There are no age restrictions or buying limitations. A Tier 2 product is an over the counter product, but has an age limited, for example, Nicorette, tobacco or plan B emergency contraception. In this case, a potential buyer must show an ID to prove they meet the age requirement. However, there is no limit on how much you can buy for Tier 2 products. Tier 1 products have the highest level of security and processing. A Tier 1 product is an over the counter product that has an age limit and requires a reporting of usage to a Federal or State agency. For example, pseudoephedrine is a Tier 1 product because it can be used to make methamphetamine. The Combat Meth Act set limits on the reasonable amount that a person can buy. A customer can only purchase 3.6 grams a day or 9 grams a month. NPLEx—National Precurser Log Exchange database was created by the Combat Meth Act. However, only a few states now require pharmacists to log purchases in the NPLEx system. One embodiment of the present invention preferably comprises a kiosk that automatically authenticates and reports the purchase of Tier 1 products. Currently, a pharmacist is supposed to authenticate with a customer's ID, get the customer's signature, check a log book and keep a log book. However, pharmacists are not required to check NPLEx in all States. There will soon be laws that require pharmacists to check NPLEx, report the attempted purchase by the purchaser, and get clearance from NPLEx for the purchase. All of this authentication, verification, reporting and clearance is preferably done at the Kiosk. Thus, no human requirement is necessary.

In one embodiment, the kiosk automatically and securely dispenses Tier 1 controlled products, age verification products, plus high "shrink" or high theft items. A pharmacy loses 5% to 7% of gross annual sales to theft each year. The kiosk of this embodiment eliminates theft while increasing sales by removing labor intensive employee operated locking display devices and cabinets for high theft items. The kiosk re-locates high shrink OTC products now behind the pharmacy counter or locked up in cases back to the OTC floor, where they can be securely sold to customers with no staff labor or assistance necessary. The kiosk also eliminates valuable pharmacist time now unnecessarily spent checking ID's, entering Tier 1 log book information and handling high value/theft OTC product sales. The kiosk can manage all customer payment processes and transactions, securely verify a customer's identity, authorize purchases through the NPLEx national database and will dispense only transactions that are approved by NPLEx. The kiosk also reduces legal liability and risk of Tier 1 non-compliance fines and sanctions.

In one embodiment of the present invention, a store employee can personally register a customer at the kiosk to verify the person's identity. The kiosk then logs and records data received back from NPLEx reporting that the transaction was checked through the NPLEx system, records customers signature, takes a picture of the customer, and also stores a picture of the user's ID front and back. ID authentication will make sure it is a legal ID and not a fake. The kiosk authentication center preferably checks the front information of the ID with the strip encoded information on the back of the ID. If anything doesn't match, the kiosk will not allow the purchase. The kiosk preferably authenticates both state or federal IDs and even passports. The kiosk allows a pharmacy to control Tier 1 products without human interaction with the customer.

In one embodiment, the present invention comprises a kiosk which can optionally be connected to an on-line registration and/or membership system for purchase of products. Users can create profiles within an on-line website wherein their personal information can be stored. Optionally, the users can associate a credit card and/or other banking information with their accounts. In one embodiment, users can create an on-line account by creating and/or obtaining a user-profile. The users can associate identification information, including but not limited government-issued identification, along with credit card and/or banking information to their account. Optionally, if the user meets all requirements for the purchase of age-specific, legislated, governmentally tracked, reported, or limited-dispense items, including but not limited to pseudoephedrine, plan B, nicotine gum, nicotine patches, and the like, the user can purchase it at the kiosk and cause it to be dispersed at the kiosk.

In one embodiment, the kiosk can be disposed within a store. In this embodiment, if the user is found to meet any necessary requirements for purchase of a product, then the product can optionally be dispensed upon payment by the user at the kiosk. Optionally, if the user elects to continue shopping, for example, by pressing a "continue shopping" icon on the display, the kiosk can generate and issue an invoice, which can optionally contain a barcode or other indicia. In this embodiment, the user can stop by the kiosk and obtain a product, continue shopping within the store, and then make a single payment for all of the goods and product purchased upon completion of shopping. When the user has finished shopping and is paying for all of the store items and the products, the cashier can enter the information from the receipt, for example by keying it in or by scanning it. In this embodiment, the kiosk can optionally be owned by an entity other than the store owner and the user can be charged a single price by the store for the total purchase of store items and kiosk items. The store can then credit a payment to the kiosk owner. Alternatively, the user can be charged twice at the completion of his or her shopping experience, once for the store purchases, and once for the kiosk purchases. In this embodiment, when the invoice is generated by the kiosk, the user's account is updated to indicate that an outstanding balance is owed toward the purchase of the dispensed products. In this embodiment, when the user pays for the purchases at the completion of his or her shopping, his or her account can be updated to indicate that no balance is owed. In one embodiment, if a user obtains the products and indicates that he or she will continue shopping, but then fails to present the invoice at the time of the final purchase or after a predetermined time period, the user's credit card or other banking information, which is stored in his or her profile, can automatically be charged and an additional late payment fee can optionally be included. In one embodiment, the kiosk can optionally include self-checkout features. In this embodiment, the user can select store items for purchase, then self-checkout through the kiosk. In this embodiment, the user can optionally also purchase products, or only store items. By providing a self-checkout feature, store owners can thus receive an additional benefit of the kiosk. Embodiments of the present invention permit a user to pre-shop, pick up, pay for, and/or pre-pay for items at the kiosk, then leave the store without having to use the resources of a cashier at all.

In one embodiment, after the user has created an on-line user account, the user can optionally shop-for and pay in advance for products. In this embodiment, a printable receipt containing a barcode or other indicia can be issued and/or created. The user can thus print the receipt, take it to a kiosk, where the information from the receipt is entered, for example by scanning it. A password, a personal identification number, or other unique identifiers, such as biometric data can be used to confirm the customer's identity and the products can be dispensed. Alternatively, a user can shop for products online, make a payment for them, travel to a kiosk, log into his or her account using a user name and pass code or other unique identifiers, and his or her products can be dispensed. Optionally, a user can determine if all or some of his or her products are in-stock at a particular kiosk, prior to traveling to that kiosk. This can be done over the Internet, telephone, and/or wirelessly, for example via a hand-held wireless device.

Optionally, the kiosk can include an electronic signature pad for capturing signatures when such are required for credit card payments and/or to comply with governmental regulations and/or laws. In one embodiment, a user can be authenticated via a live webcam or via still images obtained at the kiosk and transmitted to a reviewer and/or reviewing software remote from the kiosk. Optionally, this visual authentication can be performed each time that a user visits a kiosk, or can be done only on the user's first visit to a kiosk, or can be performed periodically, including randomly. In one embodiment, via the Internet, the user can create a username and password and insert relevant personal information, which can include but is not limited to name, address, phone number, credit card information and/or banking information. The user can then travel to a kiosk to be verified and/or to enter further biometric data that are specific to the user. Optionally, the user can quickly gain access to his or her account at a kiosk by swiping his or her identification card through a card reader and then entering a pass-code or other unique identifier.

In one embodiment, the kiosk can comprise one or more of the following:

a card reader, which can be a government-issued id reader, a credit card reader, and/or a combination thereof;

a cash bill and coin acceptor;

a speaker and microphone so a user can stand at the kiosk and interact with a call center at the kiosk. The call center can be located at the store and/or in another remote location;

a webcam;

a variety of product cards on pegs representing products that are available for purchase at the kiosk or other similar display. A user preferably retrieves a product card representing the product they would like to purchase. The user then scans the barcode on the back of the product card at the kiosk, the user then receives authorization to purchase the product, if necessary. The user can then pay for the product at the kiosk and then preferably disposes of the product card at the kiosk. The user then retrieves the actual product from the kiosk. FIGS. 30-34 illustrate a kiosk with product cards that are used to purchase products;

a door for retrieving the purchased products;

one or more storage shelves to store the products available for purchase;

the ability to report to one or more persons, and/or to one or more on-line databases the inventory status of the kiosk, preferably via a high-speed data link, which can be wired and/or wireless;

the ability to hold pre-purchased items for registered users for a specified period of time for later pickup;

the ability to issue notifications and/or reminders to users who have pre-purchased items for later pickup prior to releasing the held items back to inventory for purchase by others; and/or the ability to store one or more photographs and/or video segments of a user during an interaction with the kiosk, which can be used to later prove the user's interaction with the kiosk and/or to prosecute a user for an illegal transaction or entry attempt.

In one embodiment, authentication device hardware can include not only authentication hardware, which is physically attached to a kiosk, but can also include authentication hardware which is physically separated from a kiosk. Optionally, the authentication hardware can be controlled by a process which is separate from the processing of the kiosk's other functions.

Optionally, operation of the kiosk can be tied to product SKU's for products which require authentication, for example those substances which are not permitted to be sold to a minor. The SKU's can also be use for reporting and/or updating a local and/or national tracking database. In one embodiment, if such a product is selected for purchase, authentication hardware can then be activated for a determination of whether the purchase should be allowed or denied. The system of the present invention can then optionally log the transaction, generate a report or update any necessary control-log reporting data, and can optionally require a signature and/or picture/video from the user.

In one embodiment, the system of the present invention can track and maintain a log of each user's purchases and can optionally store images of, or information relating to, receipts generated from one or more transactions. In this embodiment, the user can optionally later retrieve the receipts and print them, so that the user need not worry about keeping physical copies of all receipts generated by interactions with kiosks. In one embodiment, for purchases made at a kiosk, which provide the user with a rebate, the system of the present invention can optionally automatically populate a rebate request with the user's required information. In this embodiment, the rebate request can optionally be submitted by the system of the present invention on behalf of the user, or the user can log onto a website and print out the populated rebate request. As with rebates, for products which require or offer warranty registration, the system of the present invention can also self-populate these forms and submit them or permit a user to print them out and submit them. The ability to automatically submit rebate requests and/or warranty information can optionally be pre-selected by a user by accessing his or her on-line profile and setting the preferences.

Embodiments of the present invention can be tied to and/or accessed by a user's cell phone. A cell phone application can be provided with generates a unique code or other identifying indicia, including but not limited to a scannable optical code, which can be presented on the user's cell phone and thus used to identify, partially or wholly, the user to a kiosk. In one embodiment an application can be provided on the user's phone such that the user can scan the barcode of a product that he or she wishes to the application would thus permit the user to easily place an order which can later be picked up a kiosk. Optionally, the users can scan or pick all desired items with a phone so that they can be purchasing the items with their phone while they shop for other items in the store. This embodiment can optionally be provided for stores that do not have a kiosk. Optionally, a phone application can be associated with one or more stores' frequent shopper and/or valued customer cards, thus permitting the customer to benefit from rewards as well as allow store to obtain the information captured by such programs.

A kiosk of one embodiment of the present invention can be located in a secure location or an unsecure location, or outside as a fully standalone machine and built in an armored fashion.

In another embodiment of the present invention, the kiosk can be used to distribute and sell a previously prescription only drug that is converted into an OTC product with conditional limitations like, for example: need to get blood tested every 4 months; need liver enzymes checked; need to follow up with doctor on a regularly scheduled basis. In this embodiment, the kiosk is preferably connected with a doctor in order to allow the doctor or pharmacist access to information from a patient requesting a purchase from the kiosk. In this embodiment, the kiosk is preferably connected with a doctor in order to allow the doctor or pharmacist access to information from a user requesting a purchase from the kiosk. The kiosk can electronically direct communications among and between users, pharmacists or pharmacy staff, doctors, health care professionals, insurance companies, governmental agencies, regulatory groups, law enforcement agencies or any other individual or agency which may benefit from or be required to be contacted or notified of the transaction. In this embodiment, the parties involved in the communications are authenticated using any secure process which can securely identify the communicating parties such as but not limited to, for example, passwords, biometrics (e.g. fingerprints, retinal scans, facial recognition, or any other similar biometric identification process), ID card, visual recognition by persons face to face, visual recognition via camera or video feed to a call center, combinations thereof or the like. Computerized approval based on pre-enrollment user identification criteria is authenticated electronically and stored on a computer onsite or offsite.

Users have the ability to securely log into a kiosk network to shop and check inventory availabilities in order to find a suitably located kiosk for product pickup. If the product desired requires purchase approval from an individual, company or agency (e.g., doctor, pharmacist, DEA, law enforcement agency, FDA, insurance carrier or any other regulatory body), the user's purchase request is processed by the kiosk computer systems and forwarded to the all relevant parties or regulatory agencies for approval and any reply to the request is sent back to the user as approved and ready to be picked up or denied. Denial may or may not include information supporting reason(s) for the denial and/or suggested remedies which the user can take to make or allow the requested product available to them.

In one embodiment of the present invention, a method comprises a process that allows a user to hold the requested product for a predetermined amount of time at a chosen kiosk, where the product is held for them until the predetermined amount of time expires. Should the product not be picked up prior to the expiration of the hold time, the product is then automatically available for purchase by others. Products put on hold for customer pickup can be pre-paid remotely or they can be paid for at time of pickup. Products may or may not require user authentication upon pickup depending on the specific product dispensing requirements set by governmental agencies, regulatory bodies or other relevant authorities.

In a non-limiting example, a user can remotely via computer, mobile communication device, phone, wireless device, mobile phone application (App) or other communication App, or physically at a kiosk, log in and authenticate themselves and request to purchase a regulated medication. This particular medication requires that the user has previously seen his doctor within the past six months and has had blood work done (or any other necessary testing necessary) to determine that the medication is safe for use by the user for a period of time (e.g. six months). The time period is preferably determined by a doctor, pharmacist or other agent/agency). A particular medication or product also can also be limited by the DEA or other regulatory body and is limited to purchase of only three grams per day or nine grams in a 30-day period. The particular product can also have a local (state, county or any other regulatory body) requirement that the user cannot have any felony drug convictions on their record. The particular product can also optionally have further limitations which require the user to answer certain questions which then further qualifies that the product is safe for their use. These questions can be anything relevant to safely and securely using the product, for example, have you consumed alcohol in the last 24 hours; are you taking certain vitamins; have you experienced headaches recently; do live at an elevation at or above 3,000 feet above sea level, combinations thereof or the like.

If the required parameters for the user's use of the medication or product are met, then the product is made available to the user for purchase and they can complete the transaction at the kiosk. If any or all of the parameters are not met, the transaction can be denied based on the parameters. The attempt to purchase the product can be communicated to any or all of the relevant persons or agencies that require notification. There are a variety of reasons for notification, some examples include but are not limited to: purchaser had a felony drug conviction and was on probation which would be revoked it they attempted to purchase any pseudophedrine products. The user's attempted purchase is denied and this attempted purchase is then communicated to law enforcement or regulatory agency who can receive all the details of the attempted purchase (e.g., picture/video, copy of ID card, biometric info or any other identifying information along with the details of the product (s) attempted to purchase). Or, an insurance company can require, as a condition of coverage eligibility that the insured cannot take certain products in order for a medication, product or service to qualify for either health insurance payment coverage, reimbursement, or other benefits. While there are an infinite number of possibilities for this, one example of this is a lung cancer patient that is receiving medications and/or rehabilitation services which are fully or partially covered and paid for by their health insurance provider. A condition of eligibility for these medications and services to the patient from their health insurance provider is that they do not consume or use products containing nicotine and that they maintain a body weight at or below a certain level as well as get their weight and blood pressure checked weekly. If any of the criteria for coverage are violated or not met insurance coverage is denied. If the nicotine products were either in the kiosk or the purchase of the nicotine products away from the kiosk require user identification and logging of their purchase into a computer database which then transmits this information to the kiosk, the purchase of nicotine products can then be communicated to the health insurance company. The user's health records, doctor, insurance carrier, and/or any other necessary party can access information that is available on the kiosk computer network and shared with the relevant parties to allow for enforcement of contractual obligations or policies. The purchase of a nicotine product can result in the denial of the health insurance company in paying for medications and or services. Further, the patient's weight and blood pressure can be tested at any number of testing facilities or at a fully automated location (e.g. pharmacy or retail location) which sends the required test results to the kiosk for analysis of the results. These parameters can be standard units of measure or customized specifically for the particular illness, health condition or patient specific.

If, for example, the patient met all the criteria but their blood pressure was outside of an acceptable range, the medication may or may not be dispensed. But the patient's care giver, health professional, doctor or pharmacist can be notified so they can take appropriate actions (approve, deny, request that the patient set an appointment with a health care professional, therapist, any other relevant person or agency, get blood work or other necessary testing, combinations thereof or the like). The intent of this is to allow for instant, specialized, high quality access to care, goods and services delivered conveniently and cost effectively while also allowing for the regulation of products, if required. The interactions and communications between the necessary parties to the transaction can be done by any and all means of secure communication.

The user can be at home and log into the kiosk computer network to make a request for a product that requires them to get tests performed (e.g., blood pressure) at any number of approved locations convenient to the user. The user can do this at a pharmacy and have the results sent to their doctor who can receive a notification electronically, e.g., on their cell phone or via email. The doctor can authenticate herself and log in to the kiosk computer network. The doctor can then approve the request and this information is sent to the user's pharmacist for review. The pharmacist can approve the product or service, check that insurance coverage is in place and authorize the transaction for the user to purchase through the kiosk computer network. All this can happen in a matter of minutes thereby eliminating the need for extra time and costs associated with the process.

An embodiment of the present invention comprises a method of regulating, controlling and distributing products comprising providing a kiosk having a user interface for receiving identification information from the user, authenticating the user information, prompting the user to request access to a regulated product, sending a regulator the user's request, receiving input from the regulator regarding the user's access to the regulated product, using the authentication information and the regulator input to determine what product and what amount of the product the user can purchase, and delivering the appropriate product and quantity of the product to the user. The method can further comprise providing an electronic application for requesting permission from a regulator for access to a product before providing the kiosk step and/or communicating with the regulator directly through the kiosk. The method of communication can be via telephone or Internet or other electronic means. The regulator can be a doctor writing a prescription, a pharmacist filling a prescription, and/or a law enforcement agent, for example, a DEA agent. This method can optionally comprise automatically sending the regulator information regarding the user after the authenticating user step. The prompting the user to request access step is preferably performed remotely. The step of sending a regulator the user's request is preferably electronic.

In one embodiment, the present invention can comprise a safe, which can be lockable and intelligent. Optionally, it can comprise user authentication of any type previously described. The safe can also maintain a log of all persons who have gained access to the safe via the user authentication. Optionally, the safe can automatically report to one or more predetermined locations and/or devices each time that a user is authenticated to gain access to the safe, or a report can be automatically delivered at a predetermined interval. For example, a daily log report can be issued. The reports can be automatically issued as a text short message service, an email notification, a phone call, a website login, and/or by updating a local or remote database.

In one embodiment, the safe can permit a spatially-present person to gain access to the safe contents by a remotely-located authenticated user electronically causing the safe to open. For example, the safe can be opened by an authenticated user through a text message, a phone call, an email, and/or by selecting an open instruction on an Internet website. Accordingly, embodiments of the present invention can be accessed via a hard-wired local area network, a wireless network, a cellular network, ZigBee or similar wireless mesh-network, the Internet, combinations thereof, and the like.

Optionally, the safe can include and/or be connected to an alarm system. The safe can optionally issue a notification when it is tampered with or when an unauthorized user attempts to access the safe. In one embodiment, one or more cameras can be disposed on or proximate to the safe. The one or more cameras can optionally take still images, and/or record video of all users attempting to access the safe and/or only some of the users, for example, only those persons who tamper with or are otherwise unauthorized to access the safe. The safe can also optionally be powered by an alternating current source, a battery power supply, a grid power supply with a battery-back-up, combinations thereof, and the like.

In one embodiment, the safe can be stored in a user's home, a public location, and/or a non-public commercial location. In one embodiment the present invention does not comprise any dispensing and/or counting ability. In one embodiment, the present invention can be interfaced with existing software.

Narcotics Cabinet

One embodiment of the present invention comprises a narcotics cabinet. The narcotics cabinet of this embodiment is easily accessible to the pharmacist employees and can be located close to their work station. The narcotics cabinet is preferably easily accessible so users can quickly fill a prescription. Currently, pharmacies have pharmaceuticals in as tight a space as possible. The narcotics cabinet preferably comprises a thin design to allow users to open the cabinet. The cabinet is preferably approximately 5 to 10 feet tall and more preferably approximately 7 feet tall. The narcotics cabinet of one embodiment is preferably substantially the same dimensions as pharmacy shelves. The narcotics cabinet is designed for a pharmacy and preferably comprises 5 to 15 shelves, and more preferably approximately 10 shelves adjustable. The shelves are preferably adjustable. The doors of the narcotics cabinet are preferably light weight enough to allow users to open and close the doors with minimum physical effort several times a day. The narcotics cabinet preferably mounts next to a user's work station for added convenience. The narcotics cabinet preferably fits into pharmacy aisles. Controlled products are preferably stored in a narcotics cabinet so they are secure when not dispensing them. The narcotics cabinet can optionally include one or more of the features described above for cabinet 10 in FIGS. 1-6. For example, the narcotics cabinet can include, but is not limited to an inventory control system, use of bar codes, logging and recording features and a time delay.

The narcotics cabinet can also optionally connect to an alarm system, have a duress feature, take a picture of a user or thief, comprise a camera inside and/or outside the cabinet, comprise a secondary security device (e.g., pepper spray) so when an unauthorized user breaches the cabinet, pepper spray is released or a high powered strobe light can go off to temporarily blind or disable an unauthorized user.

The narcotics cabinet of one embodiment of the present invention comprises a footprint of a working pharmacy. In other words, the depth of the cabinet equals the approximate depth of typical pharmacy shelves. The cabinet also preferably has double doors and a large sticker to deter potential thieves from robbing the pharmacy shelves since they will see that the controlled products are stored under lock and key.

Currently, many states do not require that controlled products be stored in a safe at night or when the pharmacy is closed. Rather, many pharmacies "disperse" or hide controlled products with over the counter products spread throughout the pharmacy so they are not all easily located in one section. The narcotics cabinet solves the problem of convenience and security. The narcotics cabinet is easily accessible for the pharmacy user, but also secures the products at night.

Breakaway Handle

One embodiment of the present invention comprises breakaway handle 70 for a safe or cabinet. In this embodiment, if a thief attempts to break into a safe or cabinet, the handle breaks off so that it is substantially flush with the rest of the cabinet. The perpetrator then has no leverage to open the safe or cabinet and most likely vacates the premises quickly. Behind the breakaway handle is preferably a washer that is flush with the cabinet. When the owner or authorized user of the cabinet discovers that the handle is missing, they can simply remove the washer and use an emergency key to open the cabinet. The safe or cabinet with the breakaway handle preferably comprises a mechanism that an authorized user can use to easily access the cabinet after the handle is broken off. For example, a user can access the cabinet using a key pad and an authorized code. In another embodiment, a user can have an emergency key to access the cabinet. The breakaway handle preferably breaks flush to the cabinet. A washer is preferably disposed within the cabinet and lays flush with the cabinet so a thief cannot access cabinet by reaching into a void space where the handle was and gain leverage to open cabinet. The owner would then come in, remove a washer that is flush with the cabinet and exposed after the handle is broken off, insert tool to get cabinet open, emergency key. The breakaway handle can comprise a spindle.

Industrial Applicability:

The invention is further illustrated by the following non-limiting example.

Example 1

This example includes example requirements and specifications for an embodiment of the present invention comprising a kiosk.

Glossary of Abbreviation

A—Amps
cm—Centimeters
DC—Direct Current
IP—Ingress Protection
IR—Infra-red
LCD—Liquid Crystal Display
M—Meters
mm—Millimeters
POC—Proof of Concept
POS—Point of Sale
psi—Pounds per square inch
UPS—Uninterruptible Power Supply
USB—Universal Serial Bus
V—Volts
W—Watts
WEEE—Waste from Electric and Electronic Equipment Industry Safety Standards The Kiosk preferably meets the following industry safety standard(s):
 UL 751 Vending Machines
 FCC, Part 15 Federal Communications Commission, Part 15
 UL Subject 2361 Custom-Built Kiosks
 MIL-STD-810F Department of Defense Test Method Standard Kiosk Description The kiosk vends various types of over the counter pharmacy and personal health products that tend to be high theft or must be verified to prevent usage for narcotics manufacturing. The kiosk uses common spiral vending trays controlled by a customer driven touch screen POS. A controller is housed in a safe located within the kiosk and provides the operational interface. The kiosk preferably maximizes off the shelf components and maximizes SKU count/qty of a customer provided product list. The POS system preferably integrates with store sales systems and the NPLEX verification system for some Tier 1 type products. Multi configuration solutions are available. All kiosk materials are preferably UL listed and FCC tested to reduce risk and cost for compliance testing.

Kiosk Architecture Overview

The physical architecture of the kiosk preferably comprise the following fundamental sub-systems:
 1. Main enclosure
 2. Display shelves
 3. Point of Sale Peripherals
 4. Spiral Vending System
 5. Delivery Conveyor and Product Access Area
 6. Power/UPS and Internet Delivery System
 7. Control Board
 8. I/O System
 9. Computing System The physical architecture of the kiosk is comprised of the following fundamental components: frame (including exterior skin), inventory and dispense system, human-machine interface, and product display system.

The frame provides mechanical stability for the kiosk. An exterior skin attaches to the frame, and provides security for the inventory stored in the kiosk as well as provides a foundation for the aesthetic appearance of the kiosk. The inventory and dispense system, which is supported by the frame, provides means for storing the product inventory and for initiating the dispense process of the products at the time of a user transaction. The product dispense system conveys and/or transports the products from the inventory area to the user collection point. The human machine interface provides all of the user interaction with the kiosk, and houses the user collection point. The product display system provides an aesthetic display of the products which are for sale in the kiosk.

Details for the hardware component requirements and subassemblies are presented in sections below.

Subsystems

This section describes and defines the electrical/electromechanical, power and communication subsystems.

External and internal power
Compute engine
Inventory storage and dispense
Product delivery
Inventory display and lighting
HMI External and Internal Power The kiosk is powered by a single 115 VAC 15-amp connection.

Compute Engine

The compute engine complies with the following minimum requirements:
a. A multiple Ghz processor speed
b. A multiple Gbyte RAM
c. 1 Tbyte hard disk capacity
d. USB communication ports. USB communication port count may be achieved by the use of external USB hubs.

Inventory Storage and Dispense

The inventory and dispense systems are controlled by a spiral vending motor controller. The controller is capable of controlling up to 160 spiral motors. The vending motor controllers communicate with the host computer via USB.

Product Dispense

The products are inventoried and dispensed using spiral dispensing:
a. Suitable products are inventoried and dispensed using conventional vending spirals.

Inventory Display and Lighting

The kiosk comprises three sections. The left and right sides are inventory display areas which display and highlight items which can be purchased from the kiosk. The left and/or right side of the kiosk is hinged and locked. The kiosk is designed such that a technician or stocker can unlock it and open it wide enough to allow the inventory shelves to be pulled out for restocking or service. Within this structure the displays shelves are mounted onto the main enclosure in a way not to impede inventory restocking.

Human Machine Interface (HMI)

The center section of the front of the machine houses the HMI and product delivery area.

The HMI is comprised of:
a. A 22" LCD display with integral touch screen.
b. A credit card reader.
c. Bio Reader.
d. 2D Scanner.
e. ID reader.

The product delivery area houses a door which slides open when the product is available for the customer to retrieve. The door is otherwise closed and is strong enough to prevent unauthorized intrusion into the kiosk.

Also present in the center section, at the top, is an advertisement monitor. This monitor is controlled from the host computer application.

Basic Operation Descriptions/Theory of Operation

The basic operation and failure mode responses are outlined below.

Normal Operation Modes

The kiosk is a self-service kiosk that allows consumers to purchase one or more of the items displayed in the product display area. The customer can browse the available products from a color imaging display that incorporates a touch screen user interface for navigation and input. This display provides information on each product available for sale within the system. Once the customer has made a selection, the kiosk software guides the customer through the credit card or other payment transaction and approval process (if necessary) for the purchase. Upon credit approval, the purchased product is extracted from the internal inventory, and placed in a customer-accessible location. Finally, a door opens allowing the customer to take the purchased item.

On the front of the kiosk, in the center, is a Point of Sale (POS) area, hereafter referred to as the human-machine interface (HMI). This HMI area contains the user interface devices required for the user transaction with the kiosk. The lower part of the HMI includes a product-access door which opens, allowing the user to remove the purchased product(s).

The normal operating modes are:
1. During normal operations, the kiosk is fully powered and connected to the Internet/Local Network.
2. All kiosk access doors are normally locked.
3. The product pickup access door is closed.
4. Operation of the kiosk is provided via the touch screen monitor and associated peripherals.
5. If power cycled, the system turns up with the stored system configuration settings.
6. Advertising/informational is displayed on monitors and touch screen when not in use
7. The locking mechanism fails in the locked position.
1. Provisions are provided to access the computing system via the Ethernet connections off the back of the kiosk.
2. The system completes all transactions that are initiated prior to a system power failure. The system includes an UPS that provides power to mandatory components required to complete a transaction started prior to the power failure. Those components include but are not limited to:
 a. Inventory system
 b. Product delivery system
 c. Internet connection
 d. Computer
3. The system does not allow any new transactions to be initiated if a power failure has occurred.

Electrical Requirements

Power System

A single system requires a single 15 amp, 120 VAC power feed. The kiosks has an Uninterruptible Power System (UPS) into which the input power is fed. The UPS provides some measure of AC power line surge/transient protection, and in the event of a power loss, enable the system to remain powered long enough to complete an in process transaction, and implement a controlled and orderly shutdown. The estimated time that the UPS has to provide power and shut down the system is ten minutes. The UPS has a communication/data link to the computer system.

The power feed includes a three wire plug for PWR, RTN and GND and connects directly to the UPS system. All AC powered devices derive their power from the UPS. DC power that is distributed from a central point to system elements elsewhere in the kiosks are accomplished with appropriate attention to current load requirements and ground loop considerations.

Power will be distributed in a safe manner with appropriate cable and wiring management, including labeling.

External Connections

The kiosks contain openings or connections for the following at a minimum:
- AC Power
- Network connectivity (Ethernet)
- Wireless connectivity TBD Control and Communications The system employs a single non-redundant computer to provide centralized management and control kiosk interface devices including the human interface display and touch panel, the audio system, the payment card reader, ID reader and scanners. The computer also interfaces and controls all of the actuators and automation elements that are part of the inventory management and dispensing system, and receives input from sensors located at strategic points throughout the system that insure the integrity of the dispensing functions and activities and the security of the system. Finally, the computer communicates remotely, via a wireless or wired internet link, with an operations center for reporting, inventory management, and maintenance and with a credit/charge/debit card center for card payment authorization.

Communication with the various devices is accomplished via technology that is cost efficient for the application and simplifies cabling considerations. Wherever possible, standard electrical and software protocols are utilized.

System Block Diagram

Figure 19:
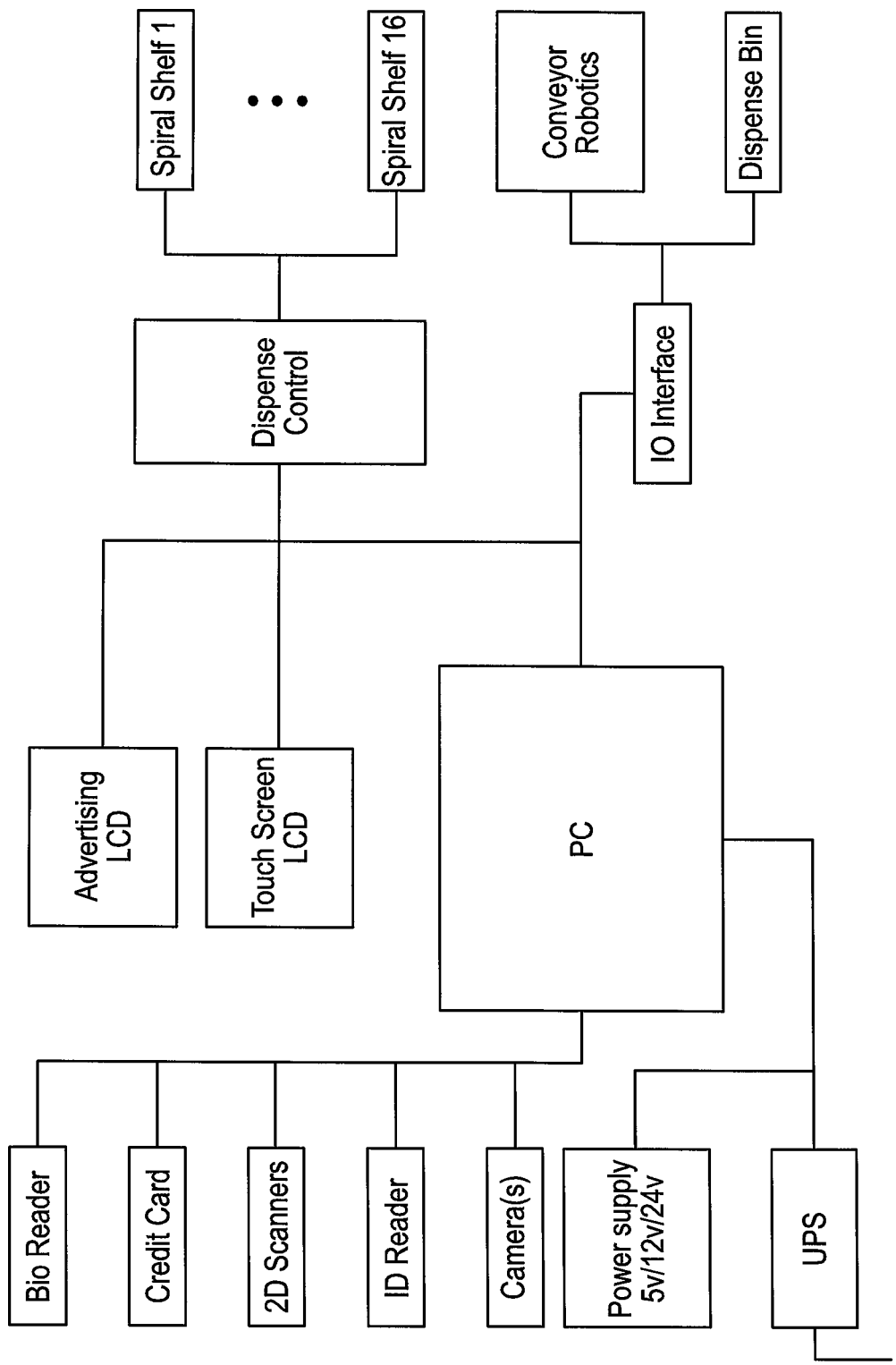
FIGS. 19-23 are flow charts which illustrate some steps which can occur when purchasing an item from a kiosk.

The diagram in FIG. 19 provides a high level description of the system.

User Interface

The User Interface is comprised of the following:
1. Touchscreen LCD
2. Credit/Debit Card Reader
3. Fingerprint Reader
4. Tethered Barcode Scanner
5. Identification Reader
6. Numerical Keypad
7. Cameras LCD Display
1. Touchscreen POS: Size: approximately 22"—16×9 aspect ratio
2. Advertising Instructional: approximately 32"—16×9 aspect ratio User Access Keys User Access Keys are utilized to control and manage access to the product vending area and POS peripherals via a SmartKey device. The key list is remotely manageable via internet.

Mechanical Requirements

Kiosk Overview

The kiosk enclosure completely encloses all components of the kiosk and provides sufficient space to house all components of the product to be vended, all peripherals and delivery hardware. The enclosure minimizes unused space within the enclosure while providing sufficient space for production and maintenance needs. The kiosk cabinet is designed to maximize the strength front of the enclosure. The enclosure provides for secure restraints of all wiring and cabling within the enclosure.

Kiosk Enclosure

Enclosure Size

The enclosure size requirements are driven by usable space on the end of aisle areas. The maximum floor footprint is approximately 48" wide (when facing the endcap end of the unit) and approximately 72" deep (requiring the removal of existing shelving units). The minimum height is approximately 50" and the maximum height is approximately 72" to ensure delivery access through standard doors.

Enclosure Materials

Cold rolled steel with a minimum thickness of approximately 1 mm is used for most of enclosure pieces (top, bottom, sides and drawer dividers). Aluminum may be used for interior structure purposes to support vending equipment and peripherals.

Enclosure Finish

The cold rolled steel pieces are powder painted per Dupont, Cardinal or Pantone color code, finish (smooth, satin or textured). Any unpainted cold rolled steel pieces is clear Zinc per ASTM B633-07, Type V, SC2. Aluminum pieces are clear Alodine per MIL-DTL-5541F.

Kiosk Product and Access

Kiosk Access

The enclosure supports being accessed daily for stocking over the kiosk's projected 7 year life.

Product Size

The maximum product size is approximately 4"×4"×3.5", there are multiple products that are smaller and allow for greater quantity and increased sku count.

Kiosk Operation/Function

Access Door Lock

The lock mechanism is an electromechanical device that is operated via an RFID key and/or commands given through the user interface. The lock(s) are located on the access doors and are selected based on cost, function and maintenance. The normal condition of mechanism is locked. The lock includes a manual override function to allow maintenance.

Door Strength

The lock and door can hold the door in place while a force is applied in a normal direction off of the door for duration of approximately 5 minutes. The lock and door can resist a load applied at a length and angle from the door front face to emulate an attack with a large screw driver or crow bar. The appearance of the door can be altered and visible damage is permissible as long as the door and lock are not compromised.

POS Configuration

The POS is configured such that the components are easily accessible for a standing adult from the outside of the kiosk. The POS/user interface includes a touchscreen LCD, a 10-digit keypad for numerical entries, a fingerprint reader, a credit card/debit card scanner, an ID scanner, a camera for still images of customer, a tethered barcode reader for receipt scanning and stocking purposes, and a microphone and speaker for American Disabilities Act fulfillment.

Vending Access

The vending (spiral tray) area is accessed via center locking, swing away double doors that will allow for access to the vending trays for restocking. The double doors are no wider than 36" each. The vending trays are outfitted with linear rollers that allow the trays to be pulled out and rest at a downward angle to facilitate restocking.

Product Delivery

After a product has been purchased, the product falls from the spiral vending trays on to a horizontal conveyor belt. The product is then made accessible from the conveyor belt to the customer via an access door that is only opened at the time of product delivery. Design measures are in place to minimize the possibility of tampering with product via the access door. To ensure the customer receives the proper product, it will be scanned and/or weighed and/or photographed before delivery to the customer.

Kiosk Enclosure Mounting Surfaces

The kiosk enclosure provides features on the bottom surface to facilitate moving the product on and off shipping palettes. Mounting provisions are provided through the bottom of the kiosk enclosure to hold the product in the required position for proper operation.

Exterior Hardware

All exterior hardware is tamper proof to ensure the security of the components and products housed within the kiosk. The kiosk remains secure during power failure. All hardware is resistant to the kiosk's environment.

Labels

The enclosure includes a label including, but not limited to the following:

The manufacturer's name, trademark, or other descriptive marking by which the organization responsible for the product can be identified.

The model number or the equivalent

The electrical rating

The date or other dating period of manufacture not exceeding any three consecutive months.

System Requirements

Figure 20:
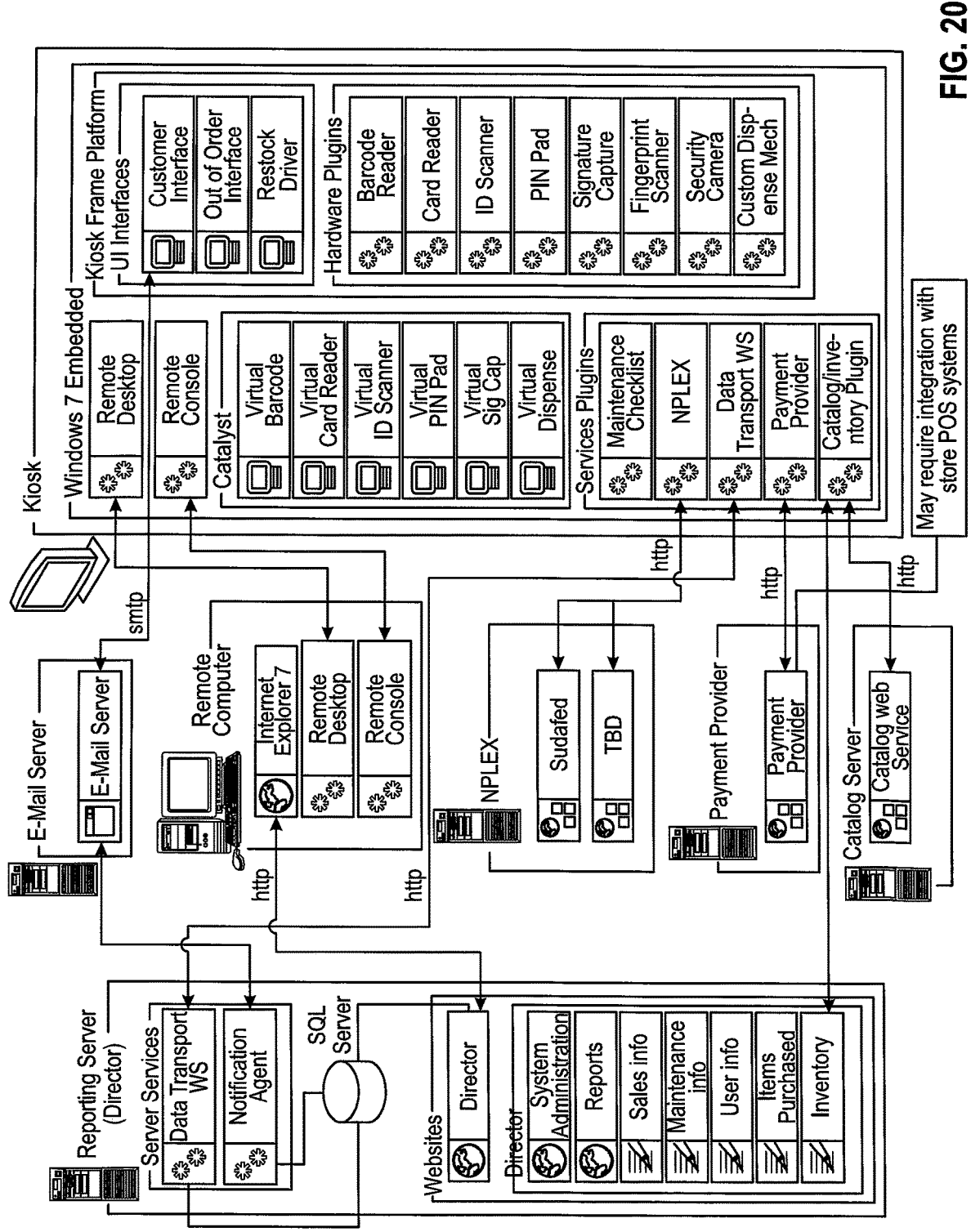

System Overview—See FIG. 20 which illustrates a system overview.

Software Use cases

Use Case—Customer Registration

Primary Actor: Customer, Call Center
    Scope: Application, Kiosk
    Level: User Goal, System Goal, Business Goal
    Precondition: None
    Main Success Scenario:
      1. At the kiosk the Customer touches the screen while the Attract Loop is playing.
      2. The kiosk displays the Main Menu
      3. The customer clicks the register new user button on the Main Menu
      4. The Pharmacist inserts the Customers Driver's License or other Government issued ID into card reader. The card reader then verifies that the ID is an authentic government issued document that has not been tampered with and is free from defects.
      5. The Pharmacist prompts the customer to scan their fingerprint
      6. Customer signs the signature pad
      7. The Pharmacist prompts the Customer to take a picture.
      8. Pharmacist reviews all data and confirms:
        a. Customer is the same person pictured on the Driver's license.
        b. The signatures all match
      9. Pharmacist approves or denies customer's registration
      10. If approved, all customer data is submitted to the backend servers, hashes created, etc.
    Extensions:
    A. Customer Registration Denied—customer cannot make a purchase at the kiosk
    B. Time limit exceeded during a transaction.
      a. Transaction is cancelled and logged.
    C. Unexpected or abnormal internal failure.
      a. System presents out of service message and the failure is logged. A kiosk administrator must service the kiosk to determine cause and to restart the application.
    D. Fatal hardware error occurs that prevent kiosk operation.
      a. System presents out of service message and the failure is logged. A kiosk administrator must service the kiosk to determine cause and to restart the application.

Use Case—Customer Purchases Tier 3 Item (Non Controlled)

Primary Actor: Customer
    Scope: Application, Kiosk
    Level: User Goal, System Goal. Business Goal
    Precondition: None
    Main Success Scenario:
      1. Customer selects item(s) from the Main Menu and adds them to the shopping cart.
      2. On the Shopping Cart screen the Customer clicks the Checkout button
      3. Kiosk reviews the items in the shopping cart and locates the item with the highest controls on it.
      4. Kiosk detects highest Tier products in cart are Tier 3
      5. Go to Use Case—Select Payment
    Extensions:
    A. Time limit exceeded during a transaction.
      a. Transaction is cancelled and logged.
    B. Unexpected or abnormal internal failure.
      a. System presents out of service message and the failure is logged. A kiosk administrator must service the kiosk to determine cause and to restart the application.
    C. Fatal hardware error occurs that prevent kiosk operation.
      a. System presents out of service message and the failure is logged. A kiosk administrator must service the kiosk to determine cause and to restart the application.

Use Case—Customer Purchases Tier 2 Item (Age Controlled)

Primary Actor: Customer
    Scope: Application, Kiosk
    Level: User Goal, System Goal, Business Goal
    Precondition: None
    Main Success Scenario:
      1. Customer selects item(s) from the Main Menu and adds them to the shopping cart.
      2. On the Shopping Cart screen the Customer clicks the Checkout button
      3. Kiosk reviews the items in the shopping cart and locates the item with the highest controls on it.
      4. Kiosk detects highest Tier products in cart are Tier 2
      5. Kiosk prompts Customer to insert Driver's License.
      6. Kiosk attempts to lookup customer account to confirm prior registration.
        a. If registration is found the kiosk will prompt the Customer to swipe their fingerprint.
        b. If registration is not found the kiosk will prompt the customer that all controlled items require the Customer to register.
      7. Kiosk will attempt to validate the fingerprint matches the Driver's License account.
        a. If fingerprint matches go to Step 8
        b. If fingerprint does not match the Kiosk will display an error message saying transaction denied and return to the shopping cart.

8. Go to Use Case—Select Payment

Extensions:

A. Time limit exceeded during a transaction.
   a. Transaction is cancelled and logged.
B. Unexpected or abnormal internal failure.
   a. System presents out of service message and the failure is logged. A kiosk administrator must service the kiosk to determine cause and to restart the application.
C. Fatal hardware error occurs that prevent kiosk operation.
   a. System presents out of service message and the failure is logged. A kiosk administrator must service the kiosk to determine cause and to restart the application.

Use Case—Customer Purchases Tier 1 Item (Individual Tracking/Control)

Primary Actor: Customer
Scope: Application, Kiosk
Level: User Goal, System Goal, Business Goal
Precondition: None
Main Success Scenario:
1. Customer selects item(s) from the Main Menu and adds them to the shopping cart.
2. On the Shopping Cart screen the Customer clicks the Checkout button
3. Kiosk reviews the items in the shopping cart and locates the item with the highest controls on it.
4. Kiosk detects highest Tier products in cart are Tier 1
5. Kiosk prompts Customer to insert Driver's License.
6. Kiosk attempts to lookup customer account to confirm prior registration.
   a. If registration is found the kiosk will prompt the Customer to swipe their fingerprint and sign the signature pad. Go to Step 7
   b. If registration is not found the kiosk will prompt the customer that all controlled items require the Customer to register and return to the Main Menu
7. Kiosk will attempt to validate the fingerprint matches the Driver's License account.
   a. If fingerprint matches go to Step 8
   b. If fingerprint does not match the Kiosk will display an error message saying transaction denied and return to the shopping cart.
8. Kiosk will validate with $3^{rd}$ party systems/databases (NPLEx) if this Customer is able to purchase the selected items.
   a. If approved go to Step 9
   b. If denied the Kiosk will display an error message to the user that they are above the legal purchase limit for the selected item and return to the Shopping Cart screen.
9. Go to Use Case—Select Payment Extensions:

A. Time limit exceeded during a transaction.
   a. Transaction is cancelled and logged.
B. Unexpected or abnormal internal failure.
   a. System presents out of service message and the failure is logged. A kiosk administrator must service the kiosk to determine cause and to restart the application.
C. Fatal hardware error occurs that prevent kiosk operation.
   a. System presents out of service message and the failure is logged. A kiosk administrator must service the kiosk to determine cause and to restart the application.

Use Case—Inventory Replenishment

Primary Actor: Store Employee
Scope: Application, Kiosk
Level: User Goal, System Goal, Business Goal
Precondition: Store Employee must be logged into Kiosk Frame with permissions to run Inventory Restock Plug-in
Main Success Scenario:
1. While the Restock Store Employee is logged into Kiosk Frame Admin Console he must click the Inventory Replenishment Plug-In Icon
2. The Kiosk will load the Restock Interface
3. The Store Employee will remove the scanner from the cradle and scan the base's barcode to associate the device.
4. The Store Employee must click the "Restock Kiosk" button to begin
5. The Store Employee will scan the barcode of an item
6. The Kiosk will display the item on the screen and show the current quantity in stock
7. The Driver will enter on the keypad of the scanner the new quantity in stock
8. The Driver repeats steps 5-7 until all items have been scanned and current quantities have been entered.
9. When all items are scanned the Store Employee must click the "Completed Restock" button on the interface.
10. The Kiosk will submit the new quantity levels to the server and optionally print a receipt for the Store Employee reflecting all new quantity levels entered.

Extensions:

A. Time limit exceeded during a transaction.
   a. Transaction is cancelled and logged.

Use Case—Select Payment

Primary Actor: Customer
Scope: Application, Kiosk
Level: User Goal, System Goal, Business Goal
Precondition: Items are in the shopping Cart, The transaction is approved, Kiosk is displaying payment selection screen
Main Success Scenario:
1. While the kiosk is displaying the payment selection screen the Customer can insert an ATM card, swipe a credit card, swipe a gift card, or scan a store reward card or value customer card, which accumulates points for shopping with the store.
2. Customer select what payment type to use:
   a. Use Case—Payment ATM
   b. Use Case—Payment Credit
   c. Use Case—Stored Value Barcode
   d. Use Case—Gift Card
3. Payment Complete.
4. Go to Email Receipt screen.
5. Customer can either enter their email address or click no receipt.

Extensions:

A. Time limit exceeded during a transaction.
   a. Transaction is cancelled and logged.

Use Case—Payment ATM

Primary Actor: Customer
Scope: Application, Kiosk
Level: User Goal, System Goal, Business Goal
Precondition: Items are in the shopping Cart, The transaction is approved, Customer selected ATM Payment
Main Success Scenario:
1. Kiosk changes from the Select Payment screen to the ATM Payment Screen 2. Customer must swipe a valid ATM card and enter their PIN code
3. Kiosk validates ATM card and PIN.
4. Payment Success—Move to Step 6
5. Payment Failure
    a. If the card is declined the kiosk will display a pop-up message saying the card was not accepted and to try another payment.
    b. Return to Use Case—Select Payment
6. Payment Complete
7. Go to Email Receipt screen
8. Customer can either enter their email address or click no receipt.

Extensions:
A. Time limit exceeded during a transaction.
    a. Transaction is cancelled and logged.

Use Case—Payment Credit
Primary Actor: Customer
Scope: Application, Kiosk
Level: User Goal, System Goal, Business Goal
Precondition: Items are in the shopping Cart, The transaction is approved, Customer select credit on Payment screen
Main Success Scenario:
1. Kiosk changes from the Select Payment screen to the Credit Payment Screen
2. Customer must swipe a valid credit card
3. Payment Plug-in validates credit card and attempts to charge the card.
4. Payment Success—Move to Step 6
5. Payment Failure
    a. If the card is declined the kiosk will display a pop-up message saying the card was not accepted and to try another payment.
    b. Return to Use Case—Select Payment
6. Payment Complete
7. Go to Email Receipt screen
8. Customer can either enter their email address or click no receipt.

Extensions:
A. Time limit exceeded during a transaction.
    a. Transaction is cancelled and logged.

Use Case—Scanning Value Card or Reward Card
Primary Actor: Customer
Scope: Application, Kiosk
Level: User Goal, System Goal, Business Goal
Precondition: Items are in the shopping Cart, The transaction is approved, Customer selects if they have a reward card
Main Success Scenario:
1. Kiosk changes from the Select Payment screen to the Reward Card Screen
2. Customer must scan the barcode on a reward card
3. Payment Plug-in validates stored reward card against the stored reward card backend servers and determines how much "reward" the customer has on the card.
4. Reward points are then added to the card for the purchase.
5. Payment Complete
6. Go to Email Receipt screen
7. Customer can either enter their email address or click no receipt.

Extensions:
A. Time limit exceeded during a transaction.
    a. Transaction is cancelled and logged.

Use Case—Payment Gift Card
Primary Actor: Customer
Scope: Application, Kiosk
Level: User Goal, System Goal, Business Goal
Precondition: Items are in the shopping Cart, The transaction is approved, Customer select Gift Card on Payment screen
Main Success Scenario:
1. Kiosk changes from the Select Payment screen to the Gift Card Payment Screen
2. Customer must scan the barcode on a stored value card
3. Payment Plug-in validates gift card against the stored value backend servers and determines how much value remains on the card.
4. Card value is greater than the shopping cart total due.
5. Card value is less than the shopping cart total due.
    a. The value of the stored value card is subtracted from the shopping cart total.
    b. Return to Use Case—Select Payment with the new lowered total due
6. Payment Complete
7. Go to Email Receipt screen
8. Customer can either enter their email address or click no receipt.

Extensions:
A. Time limit exceeded during a transaction.
    a. Transaction is cancelled and logged.

Software Requirements
Reporting
Sales—Sales transaction and Inventory Levels
Reconciliation Report
Errors—HW, SW, Network, UPS engaged, Credit Card (Defined in Detailed Design Phase)
Warnings—Door open
Service—Login, what did you do, log, maintenance reminder
Remote Control
Desktop Control
    This tool allows technicians to remotely interact with the kiosk in real time.
Remote Console
    This tool allows technicians to make configuration changes and perform maintenance tasks on the kiosk via a console that does not take over the kiosk screen.
Customer/Administrative Features:
Customer Features
Purchase
    The kiosk software and hardware allows a customer to purchase controlled over the counter medicines and high theft drug stores items from a self service kiosk. The kiosk can validate the age of the person and/or their eligibility to purchase some medications. When approved for the purchase, the kiosk dispenses the items.
Customer Registration
    In order to purchase controlled over the counter drugs or age controlled items all users must register with the system prior to purchasing items. Registration must be done at the kiosk and approved by the registration call center or other onsite registration personnel to include store employees. During registration the customer will insert a driver's license, give a finger print scan, give a signature, or enter a password and get a picture taken. The call center is responsible to validate all the submitted data matches with the picture.
Restock Driver Features
Inventory Restock An employee of the store chain hosting the kiosk performs all restocking events. The employee must replenish the items for sale at the kiosk and record everything at each kiosk location. The kiosk software allows the employee to scan the items and report quantities of each in stock at the end of a restock event.

Administrative Features

Transaction Reporting

The kiosk software records and reports all transactions that occur at the kiosk. This includes sales, inventory adjustments, and inventory restocks. Any additional personal information that was collected to authorize the sale is recorded as well.

Usage Reporting

The kiosk software records and reports all software usage of the user interface. This detailed information includes all button clicks of the interface. The data recorded is used for customer usage analysis and to improve the system. Note that custom reports are required for data analysis.

System Monitoring

The kiosk software records and reports all available information regarding the health of the kiosk hardware. This includes status of the bill acceptor, card reader, printer (if used), and network connection. Some hardware does not allow status polling such as the touch screen.

Director Management Server

The backend management server allows for remote administration of the kiosk and gives detailed reporting information.

User Classes and Characteristics

Customer

This user group consists of users of all education levels and all technical expertise levels. These users also have 1st time users and repeat users, so the system is easy for 1st time user and not slow down the repeat users.

Kiosk Stocker

This user group consists of store employees that are trained on the system to perform inventory adjustments and inventory restocks.

Call Center Agent

This user group consists of trained employees that review and approve all new customer registrations.

Store Manager

This user group consists of trained store managers who can override transactions with detailed causes.

Installer

This user group consists of trained hardware and software installers who perform the site survey, construct the kiosk, and test the software configuration.

On Site Technician

This user group comprises of trained workers, who may be outsourced, that perform hardware and software repairs on the kiosk.

Remote Technician

This user group consists of workers that are specially trained on the kiosk management software to perform remote maintenance and configuration of the kiosks.

Developers of the Kiosk

This user group consists of employees and stock holders of the developers of the kiosk.

Design and Implementation Constraints

1. The Kiosk supports at least the English language
2. The Kiosk contains a UPS to allow for a graceful shutdown of the system in the event of a power failure.

User Documentation
  Installation Guide
  Troubleshooting Guide
  Administration Guide
  Initialization (SW Setup) Guide
  Hardware Design Documentation
  Functional Requirements Specifications Document (FRS)

Assumptions and Dependencies
  Network Dependencies:
    Assumes the kiosk has a high speed, always on, internet connection.
    Assumes the kiosk has outbound access on TCP port 80 to the Director server
    Assumes the Director server is hosted by the customer in production.
    Assumes the kiosk allows inbound access on TCP ports 5900 and 7667. This may require a public IP address or port forwarding to be setup at the network layer.
  Software Dependencies on Kiosk with Full PC head unit:
    Windows XP/Windows 7 Embedded
    Microsoft .NET Frameworks 1.1, 2.0, & 3.5
    PC with 2 Ghz+ Processor, 512 MB Ram, 40 GB HD, and video card with min resolution of 1024×768

External Interface Requirements

User Interfaces (UI)

Figure 21:
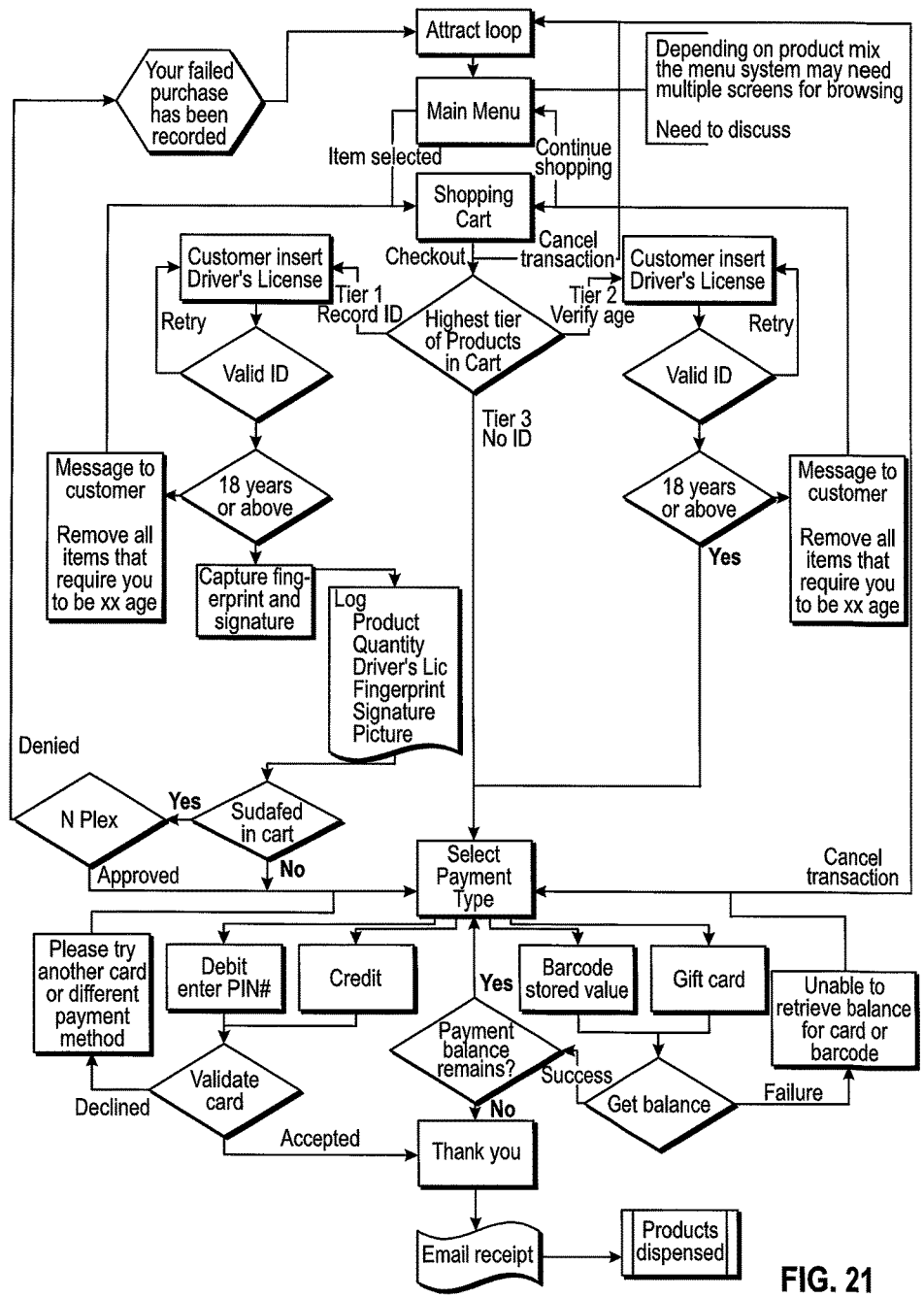

Customer UI Flow—See FIG. 21 which illustrate a customer UI flow

Figure 22:
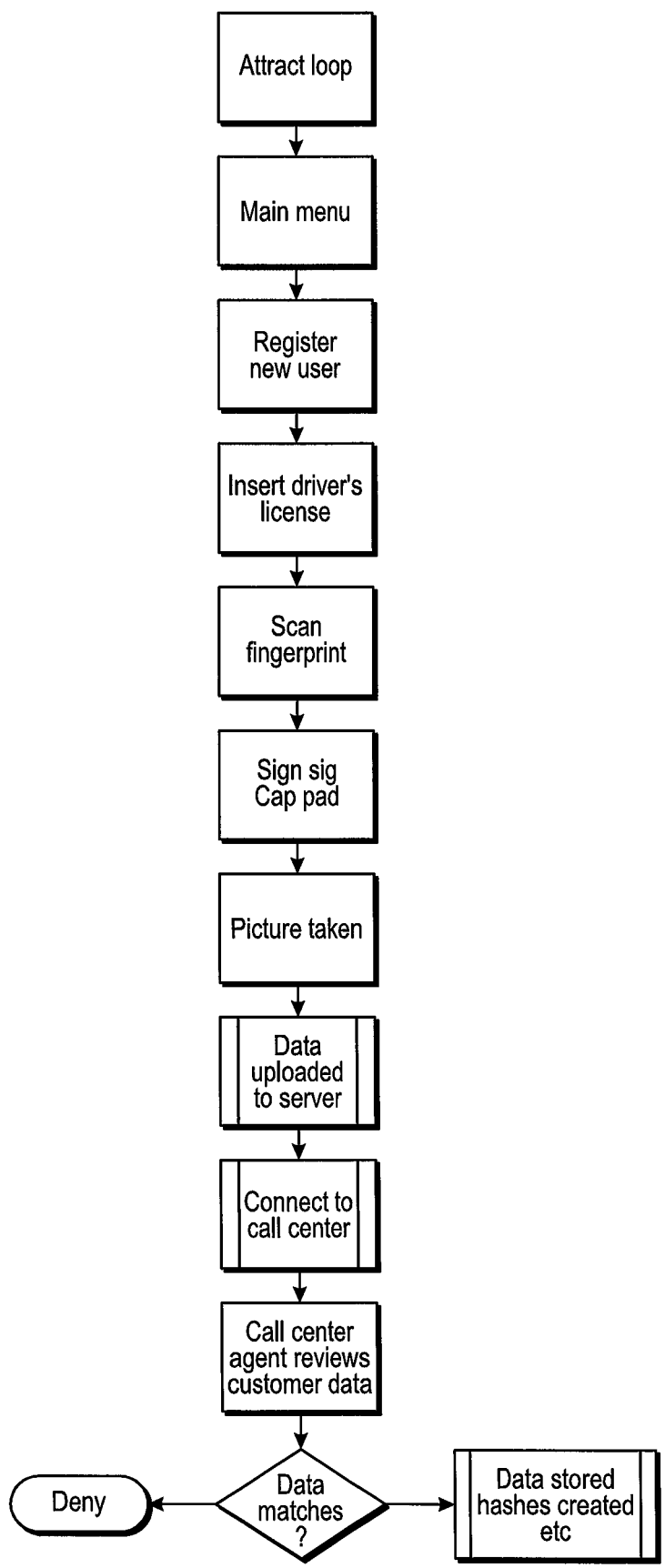
Figure 23:
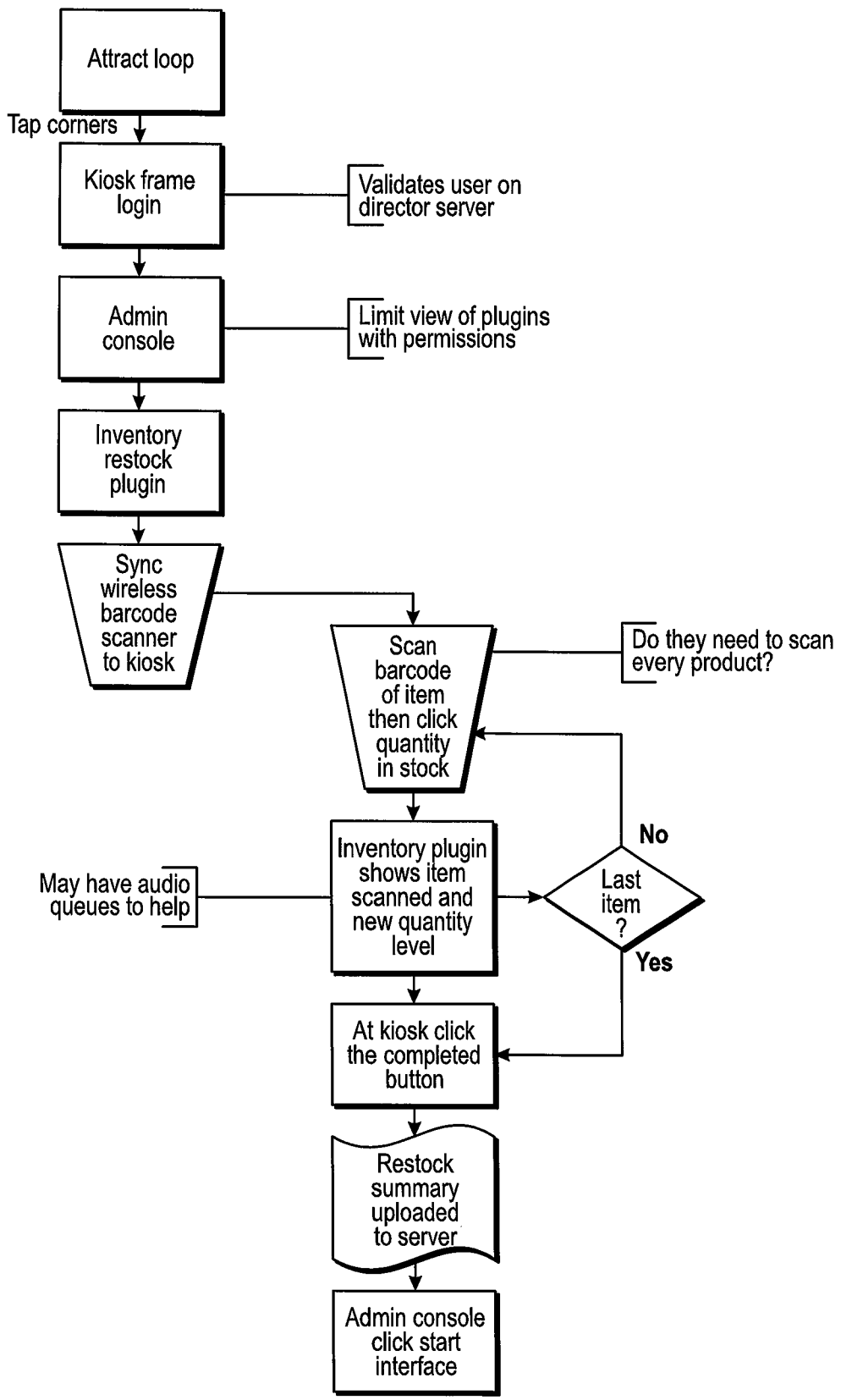
Figure 24:
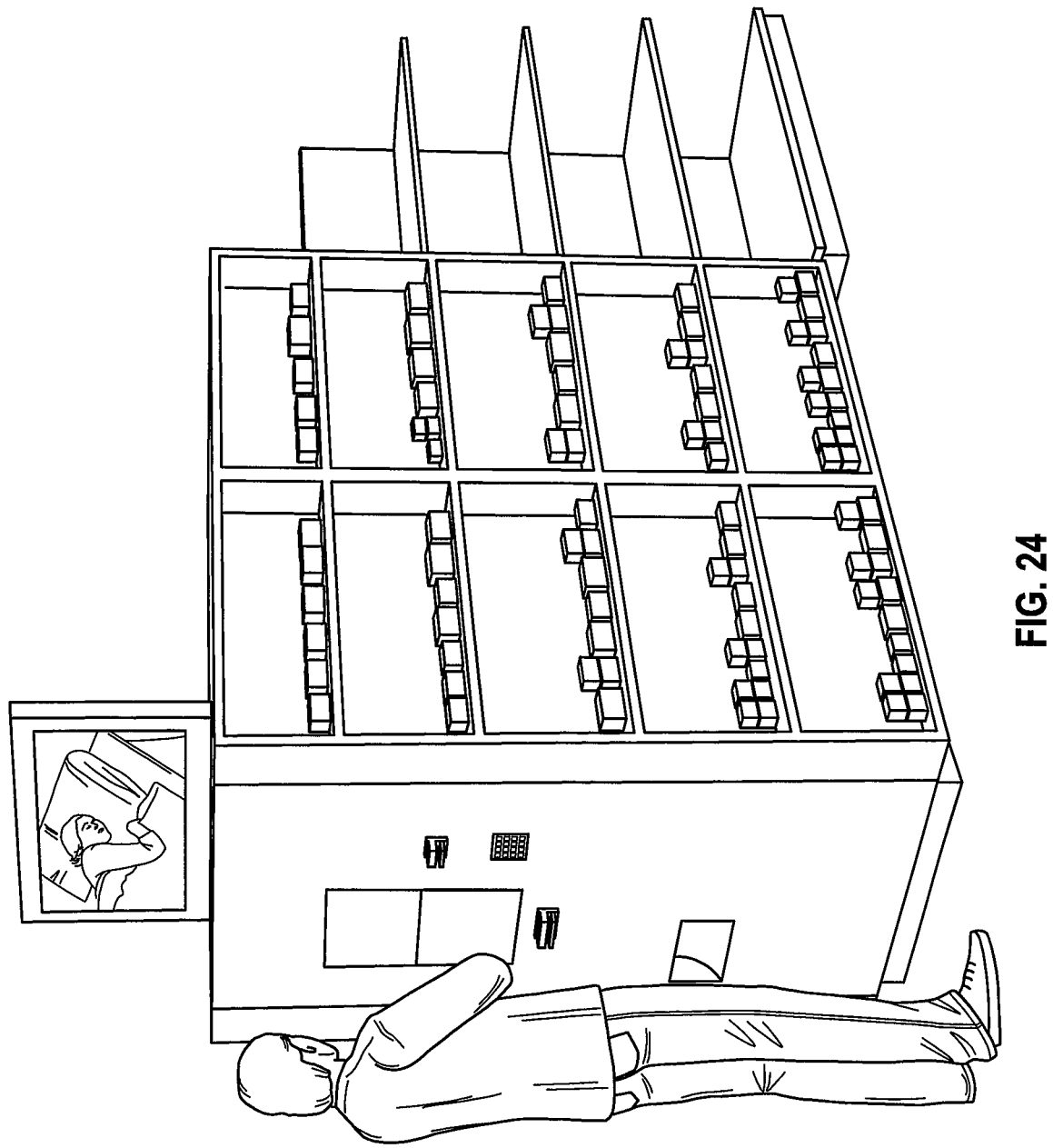
FIGS. 24-29 illustrate various embodiments of kiosks.
Figure 25:
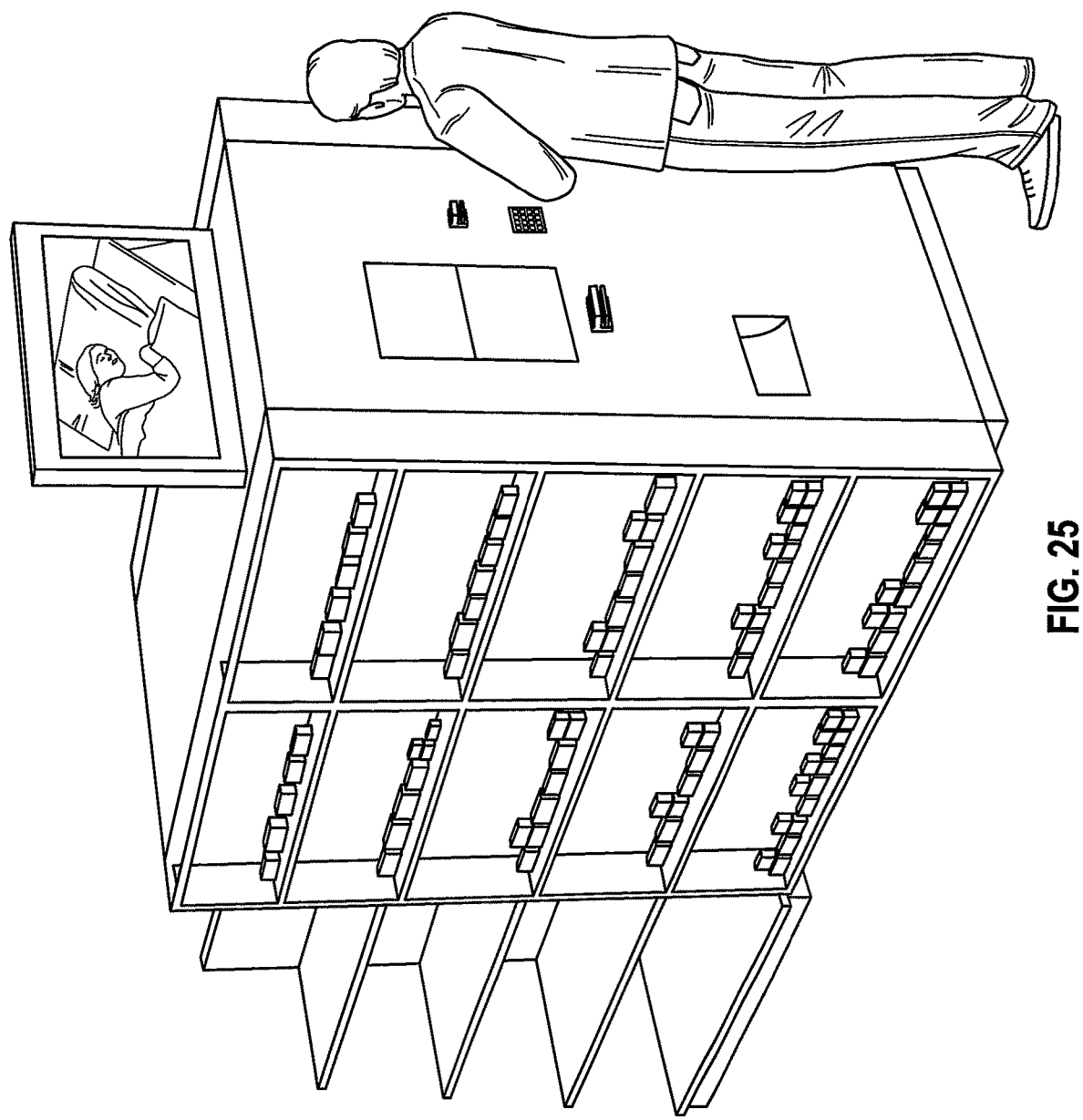
Figure 26:
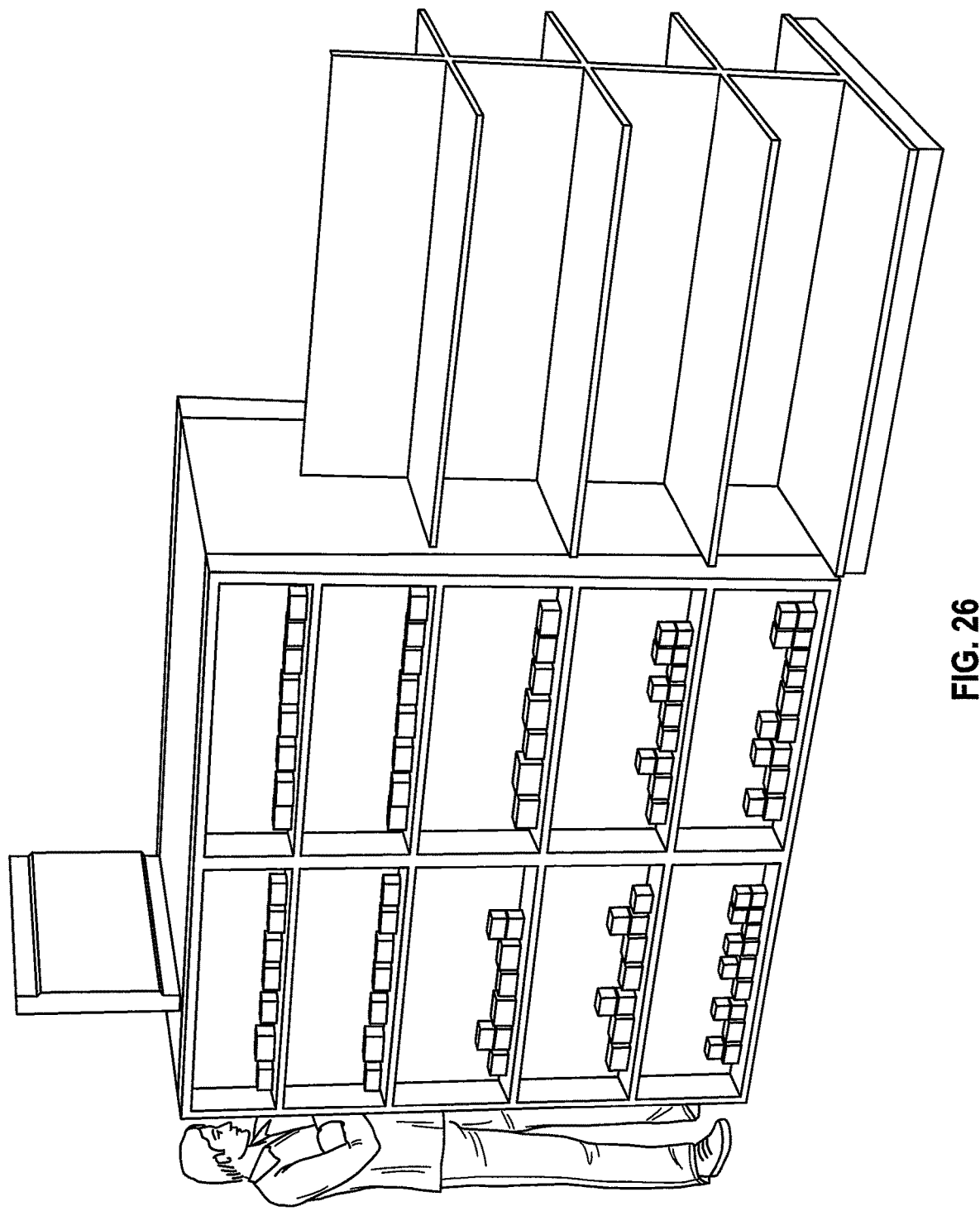
Figure 27:
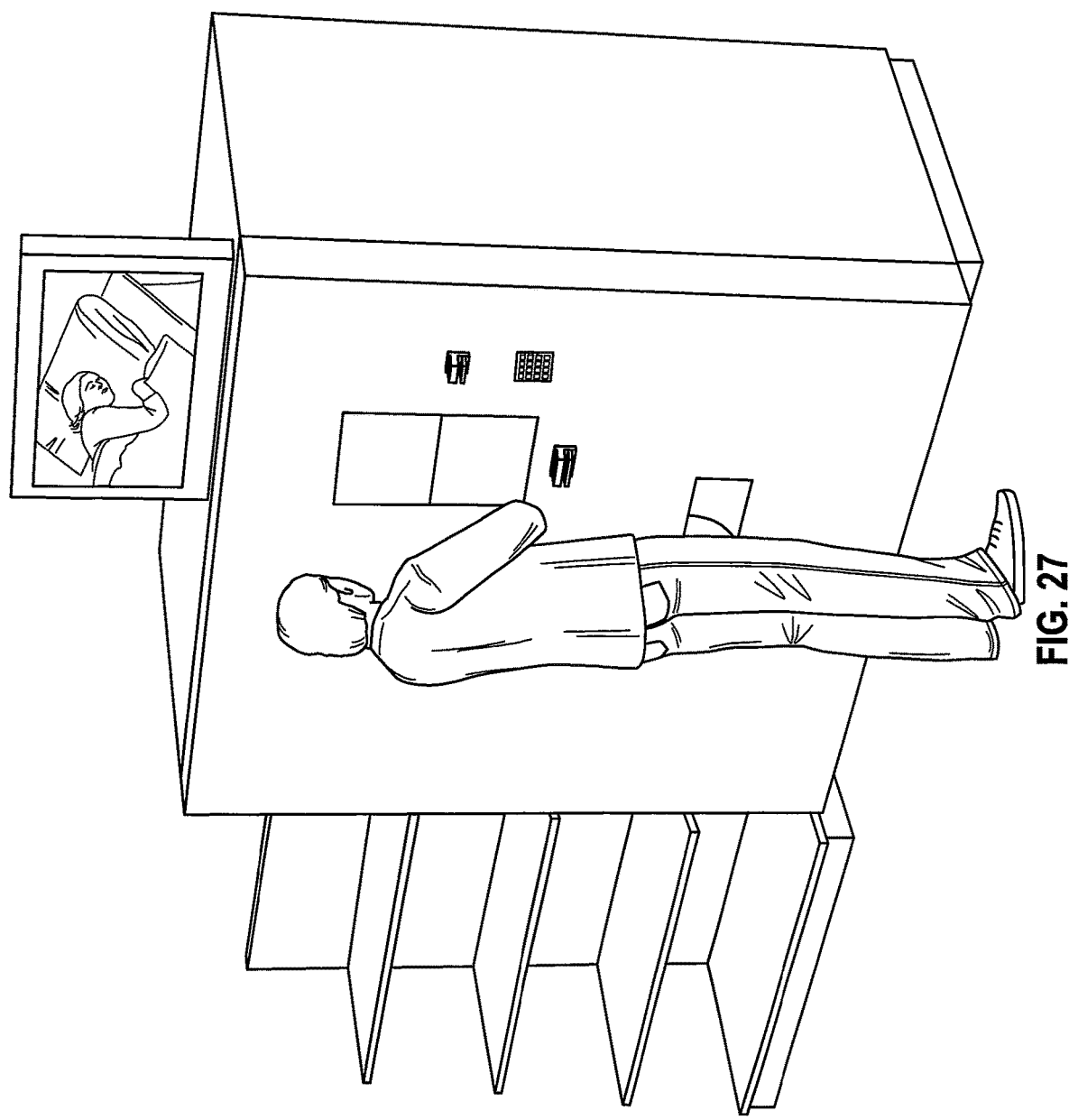
Figure 28:
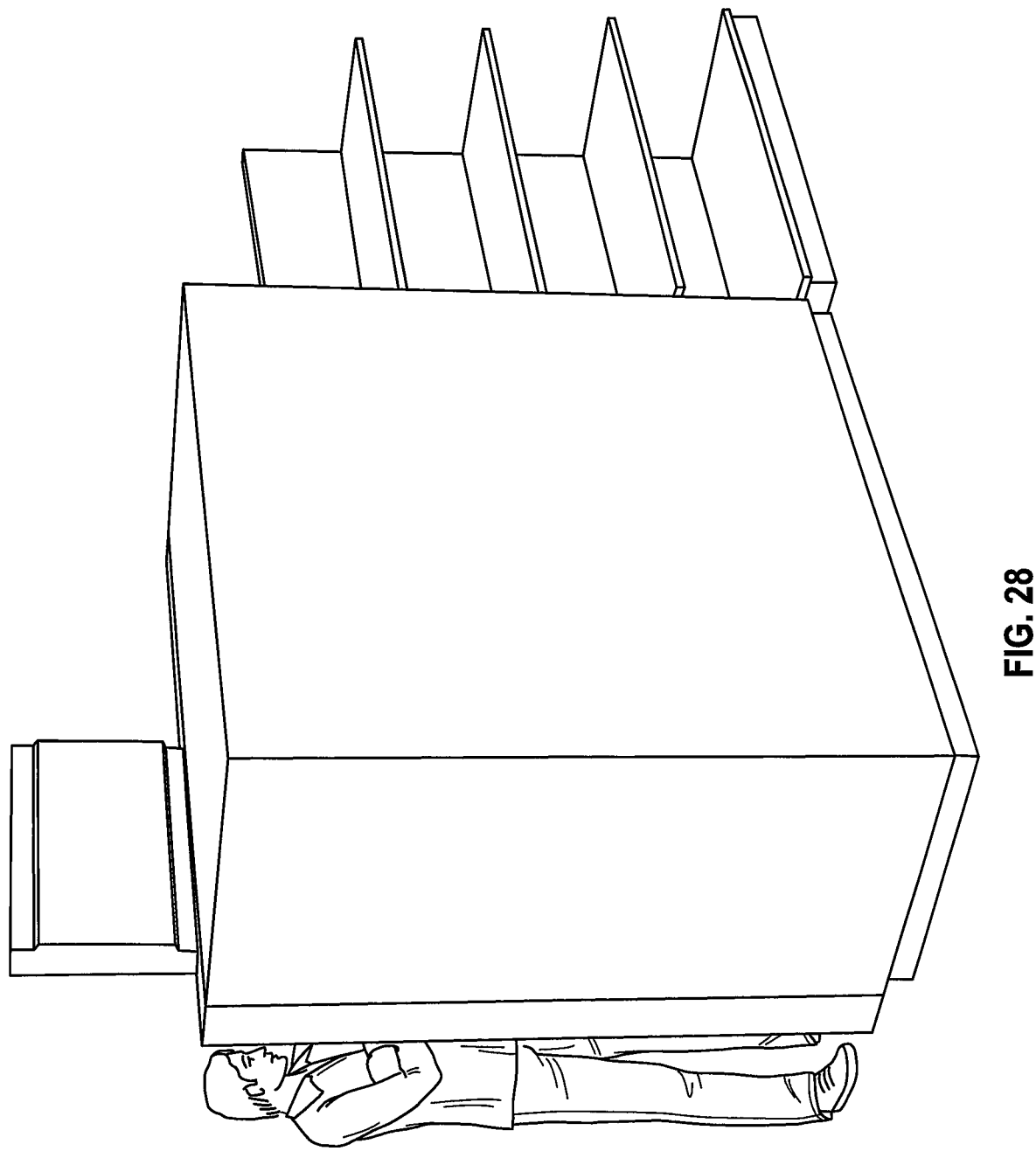
Figure 29:
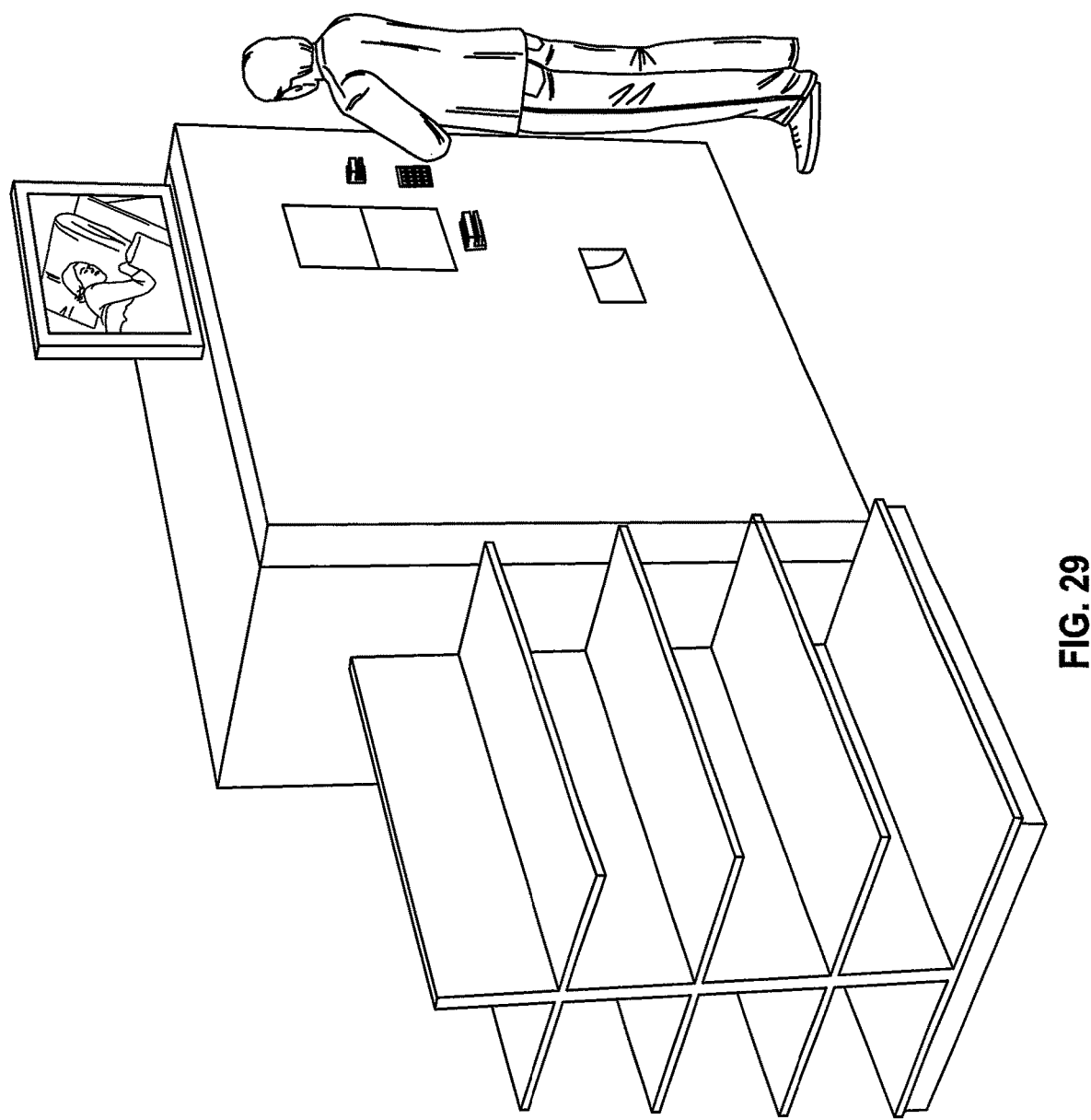
Figure 30:
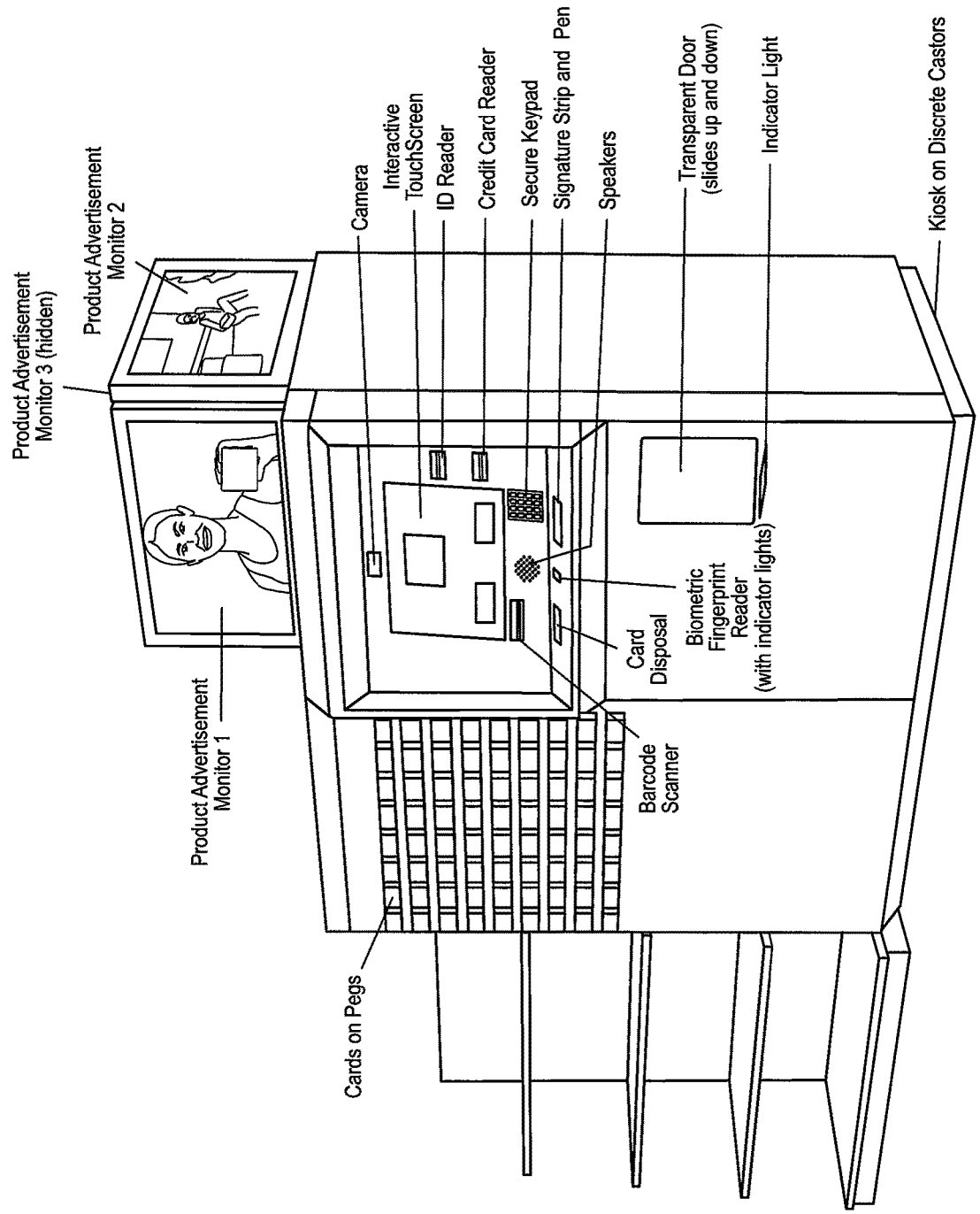
FIGS. 30-34 illustrate various embodiments of kiosks using product cards on pegs to purchase products.
Figure 31:
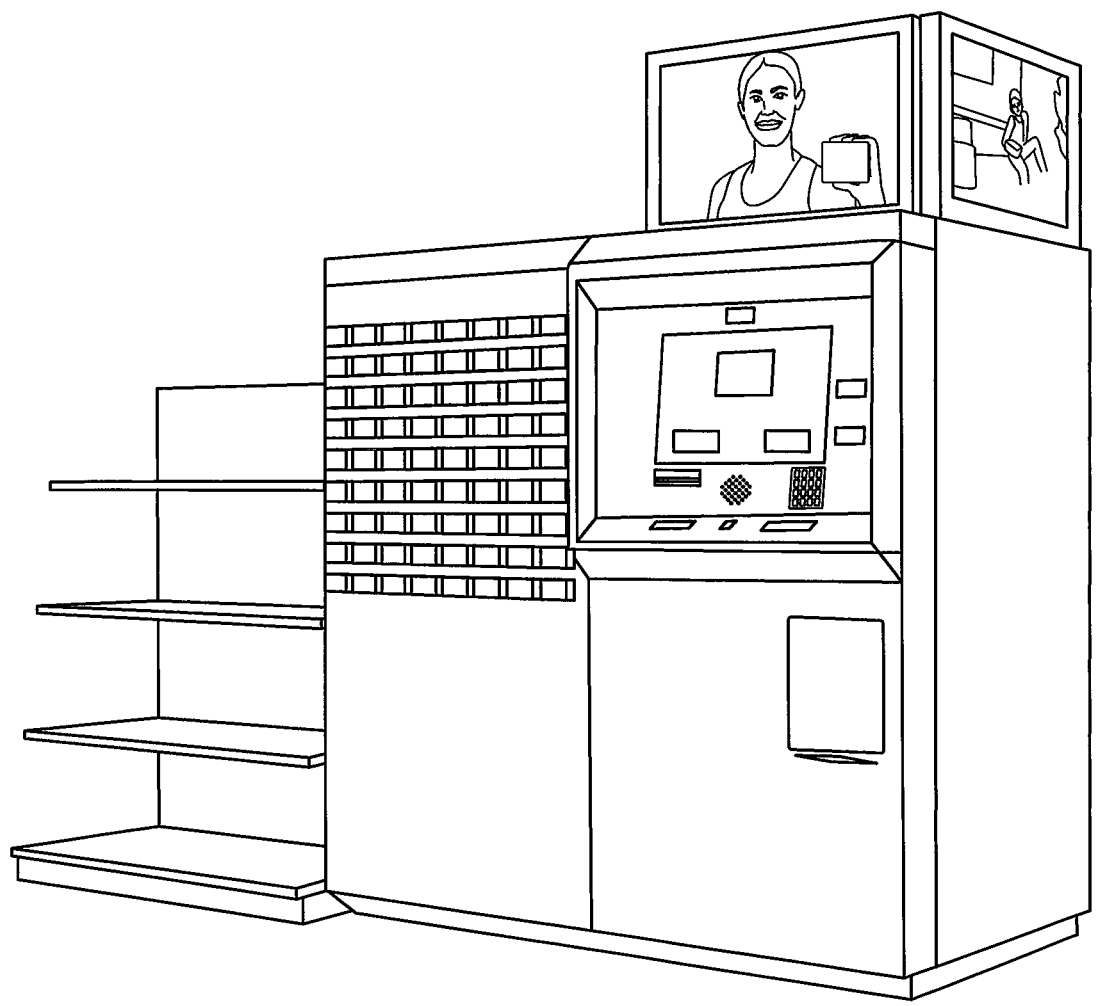
Figure 32:
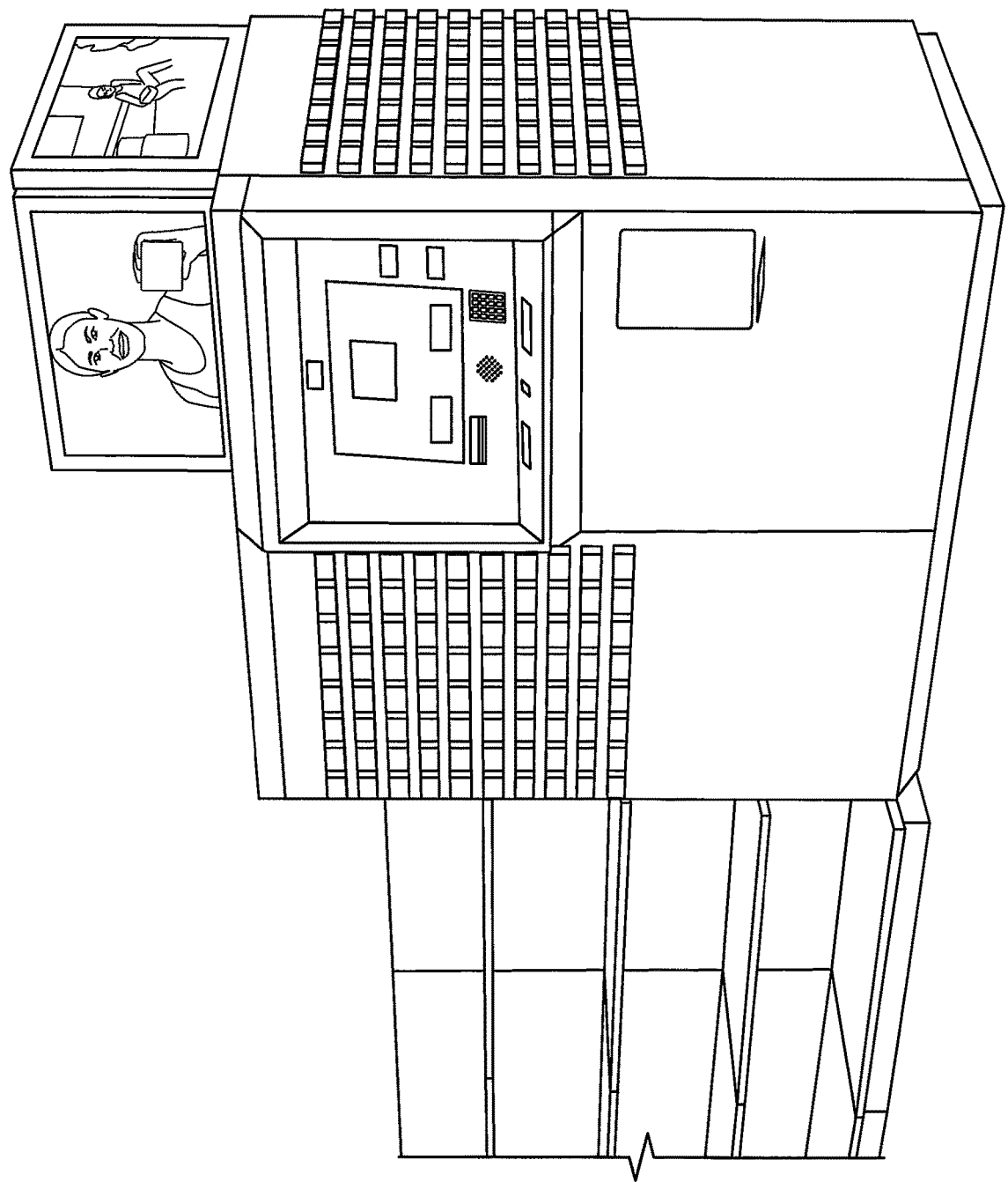
Figure 33:
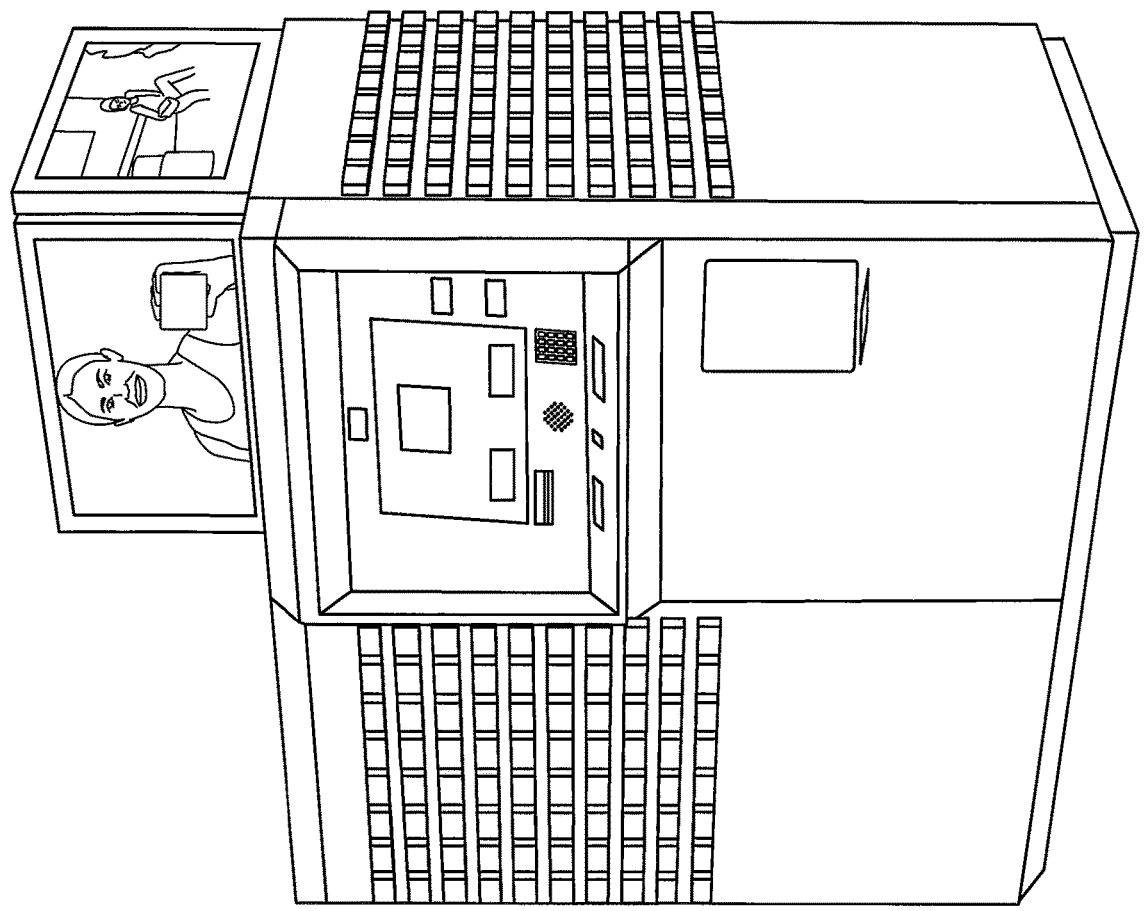
Figure 34:
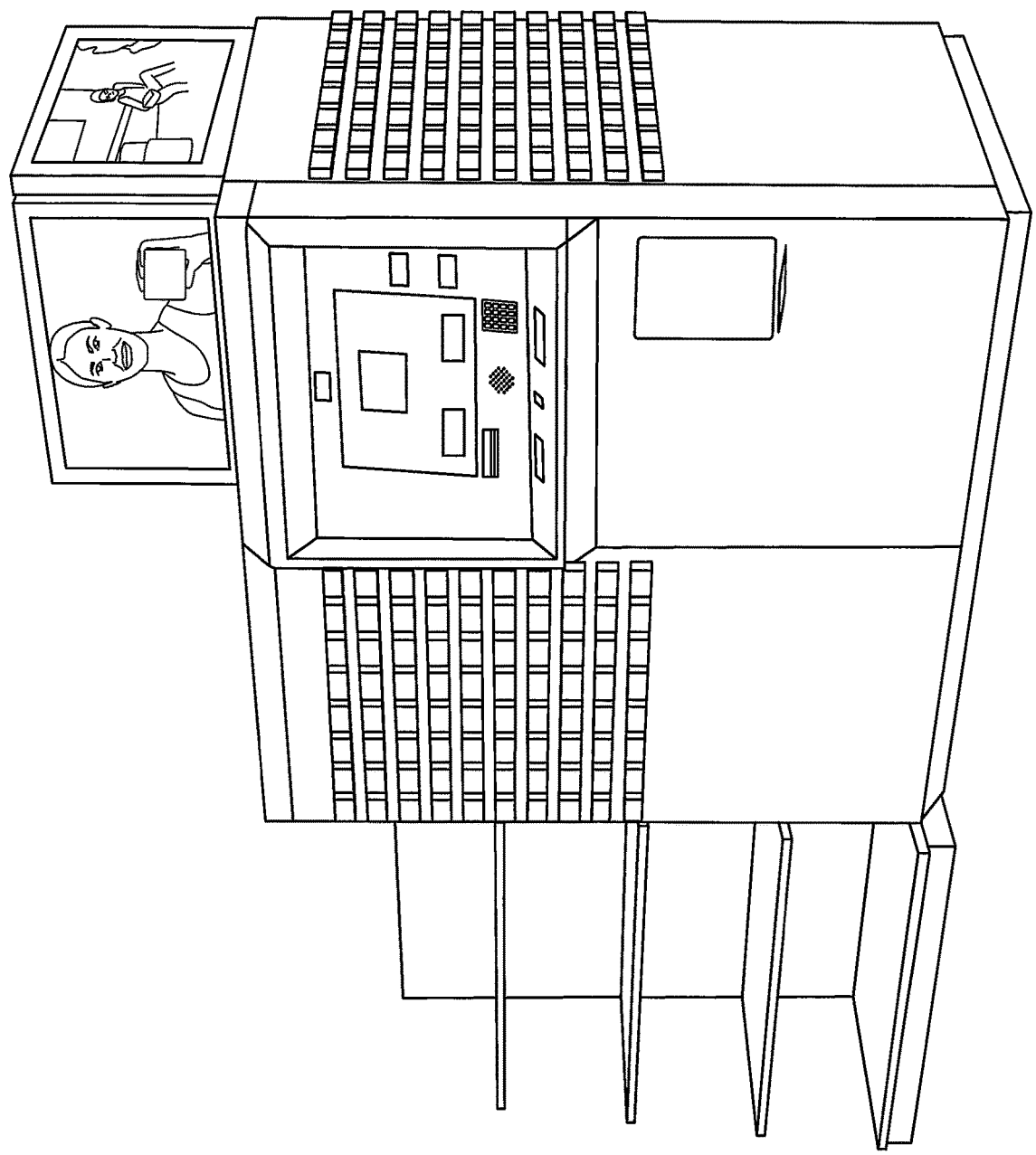

Customer Registration—See FIG. 22 which illustrates a customer registration flow Inventory Restock—See FIG. 23 which illustrates an inventory restock flow Hardware Interfaces The major components of the kiosk include but are not limited to, enclosure, PC, touchscreen, UPS, card reader, PIN pad, signature pad, ID scanner, fingerprint scanner, barcode reader, dispense mechanism, security camera, and locks.

Alarms

There are alarm requirements for the Product.

Product Maintenance

Maintenance

The expected maintenance time is 1 to 2 hours.

Field Replaceable Units (FRU)/Provisionable Options

The Product is designed to allow service and maintenance personnel access to FRU's and the ability to service or replace the FRU's at the installed site. The following is a list of at least some of the FRU components. Additional FRUs may be added during the detailed design phase if required.

| FRU# | Description |
| --- | --- |
| 1 | Cables |
| 2 | Controller PCBA |
| 3 | Vending Motors/Spirals/Dividers |
| 4 | Lock Mechanism |
| 5 | Touch screen and most POS components. |

Safety

The kiosk is designed to meet UL 751 and is free of hazards, such as sharp edges, burrs, etc., that could present a safety hazard to personnel involved in the assembly, installation, use or maintenance of the enclosure. The exposed surfaces of the enclosure do not represent a hazard to the public or craftspersons. Surface temperatures of the exterior of the cabinet meet the following requirements: metallic surfaces shall not exceed 70° C. (158° F.) and polymeric surfaces shall not exceed 130° C. (266° F.).

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention can be obvious to those skilled in the art and it is intended to cover in the appended claims all such modifications and equivalents. The entire disclosures of all references, applications, patents.

What is claimed is:

1. An automated medication dispensing cabinet comprising:
   a lockable cabinet;
   an automated medication counter;
   one or more electronic locking control mechanisms for one or more dispensing mechanisms and containment mechanisms;
   said one or more electronic locking control mechanisms comprising a programmable time delay for at least one of dispensing a medication and opening of said containment mechanisms, said one or more electronic locking control mechanisms configured to permit authorization requirements for entry;
   an electronic inventory control;
   one or more control electronics configured to provide electronic control and recordation of access to said automated medication dispensing cabinet, said electronic control and recordation of access comprising a plurality of identifiers, and capable of reporting access to said automated medication dispensing cabinet;
   said one or more control electronics further configured such that when a medication is scanned for a manually filled prescription, said control electronics both verify that a proper stock bottle has been selected and create a log entry that the stock bottle was removed from said lockable cabinet;
   one or more alarms;
   one or more electronics configured to provide one or more authentication steps for access; and
   one or more electronic access controllers.

2. The automated medication dispensing cabinet of claim 1 further comprising a biometric input device.

3. The automated medication dispensing cabinet of claim 2 wherein said biometric input device comprises a fingerprint reader.

4. The automated medication dispensing cabinet of claim 1 further comprising a keypad.

5. The automated medication dispensing cabinet of claim 1 further comprising a touchscreen.

6. The automated medication dispensing cabinet of claim 1 wherein said automated medication dispensing cabinet is connectable to an alarm system.

7. The automated medication dispensing cabinet of claim 1 wherein said lockable cabinet comprises a plurality of sections.

8. The automated medication dispensing cabinet of claim 7 wherein one or more of said plurality of sections can be lockable.

9. The automated medication dispensing cabinet of claim 1 wherein said one or more dispensing mechanisms are configured to be capable of dispensing at least one of tablet type medication and caplet type medication.

10. The automated medication dispensing cabinet of claim 1 wherein said containment mechanisms further comprising one or more back stock storage containment mechanisms.

11. The automated medication dispensing cabinet of claim 1 wherein said one or more alarms are capable of providing a silent alarm.

12. An automated medication cabinet comprising:
    a lockable cabinet;
    one or more electronic locking control mechanisms configured to provide locking control for one or more containment mechanisms;
    said one or more electronic locking control mechanisms comprising a programmable time delay for at least one of dispensing a medication from said one or more dispensing mechanisms and opening of said one or more containment mechanisms of said automated medication cabinet;
    said one or more electronic locking control mechanisms maintaining a user access log;
    said one or more electronic locking control mechanisms configured to permit authorization that requires one or more authentication steps;
    one or more electronic access controllers;
    one or more electronics configured to record and log user access into a reporting system, said one or more electronics configured to record and log user access into a reporting system and configured to provide at least one of logging, recording, and time-stamping user access;
    the one or more electronics further configured such that when a medication is scanned for a manually filled prescription, the one or more electronics both verify that a proper stock bottle has been selected and create a log entry that the stock bottle was removed from the lockable cabinet;
    an automated medication counter; and
    said lockable cabinet further comprising one or more alarms.

13. The automated medication cabinet of claim 12 wherein said automated medication cabinet is connectable to an alarm system.

14. The automated medication cabinet of claim 12 further comprising a biometric input device.

15. The automated medication cabinet of claim 14 wherein said biometric input device comprises a fingerprint reader.

16. The automated medication cabinet of claim 12 further comprising a keypad.

17. The automated medication cabinet of claim 12 further comprising a touchscreen.

18. The automated medication cabinet of claim 12 wherein said dispensing mechanisms are configured to dispense at least one of tablets and caplets.

19. The automated medication cabinet of claim 12 wherein said one or more alarms are either silent or non-silent.

20. The automated medication cabinet of claim 12 wherein said one or more dispensing mechanisms and containment mechanisms are configured to provide storage of back stock.

21. A method for providing automated medication delivery comprising:
    providing a lockable cabinet;
    disposing an automated medication counter in the lockable cabinet;
    disposing one or more dispensers in the lockable cabinet;
    disposing an electronic locking control mechanism in the lockable cabinet;

configuring the electronic locking control mechanism to provide a programmable time delay for at least one of dispensing a medication and opening of the lockable cabinet;
configuring the electronic locking control mechanism to permit authorized personnel to make changes to the programmable time delay;
providing an electronic access controller;
configuring the electronic access controller to permit at least one of logging of user drug access, recording user drug access, and time-stamping user drug access;
providing a reporting system;
configuring the electronic access controller to require one or more authentication mechanisms;
providing an alarm system;
when a medication is scanned for a manually filled prescription, the automated medication delivery verifying that a proper stock bottle has been selected and creating a log entry that the stock bottle was removed from the lockable cabinet; and
configuring the alarm system.

22. The method of claim 21 wherein configuring the electronic locking control mechanism to provide a programmable time delay comprises configuring the electronic locking control mechanism to initiate the time delay before dispensing the medication.

23. The method of claim 21 wherein configuring the electronic locking control mechanism to provide a programmable time delay comprises configuring the electronic locking control mechanism to initiate the time delay after dispensing the medication.

24. The method of claim 21 wherein configuring the electronic locking control mechanism to provide a programmable time delay comprises configuring the electronic locking control mechanism to initiate the time delay before allowing the lockable cabinet to be opened.

25. The method of claim 21 further comprising maintaining a user access log.

26. The method of claim 25 wherein maintaining a user access log comprises the use of one or more user codes.

27. The method for providing automated medication delivery of claim 21 wherein said disposing one or more dispensers further comprises dispensers that are capable of dispensing at least one of tablets and caplets.

28. The method for providing automated medication delivery of claim 21 further comprising providing at least one back stock containment mechanism in the lockable cabinet.

29. The method for providing automated medication delivery of claim 21 further comprising configuring the alarm system to permit silent or non-silent alarms.

* * * * *